United States Patent
Fan et al.

(10) Patent No.: US 11,702,687 B2
(45) Date of Patent: Jul. 18, 2023

(54) MULTIPLEX DETECTION OF INTRACELLULAR OR SURFACE MOLECULAR TARGETS IN SINGLE CELLS

(71) Applicant: Yale University, New Haven, CT (US)

(72) Inventors: Rong Fan, Cheshire, CT (US); Yao Lu, New Haven, CT (US); Nayi Wang, New Haven, CT (US)

(73) Assignee: Yale University, New Haven, CT (US)

( * ) Notice: Subject to any disclaimer, the term of this patent is extended or adjusted under 35 U.S.C. 154(b) by 690 days.

(21) Appl. No.: 16/319,188

(22) PCT Filed: Jul. 17, 2017

(86) PCT No.: PCT/US2017/042360
§ 371 (c)(1),
(2) Date: Jan. 18, 2019

(87) PCT Pub. No.: WO2018/017469
PCT Pub. Date: Jan. 25, 2018

(65) Prior Publication Data
US 2019/0276880 A1    Sep. 12, 2019

Related U.S. Application Data

(60) Provisional application No. 62/363,696, filed on Jul. 18, 2016.

(51) Int. Cl.
*C12Q 1/6837* (2018.01)
*C12Q 1/6809* (2018.01)

(52) U.S. Cl.
CPC .......... *C12Q 1/6837* (2013.01); *C12Q 1/6809* (2013.01)

(58) Field of Classification Search
CPC ........................... C12Q 1/6837; C12Q 1/6809
See application file for complete search history.

(56) References Cited

U.S. PATENT DOCUMENTS

2016/0054308 A1    2/2016    Guo et al.

FOREIGN PATENT DOCUMENTS

WO    WO 2014/200767 A1    12/2014
WO    WO 2015/044428 A1    4/2015

OTHER PUBLICATIONS

Li et al., Detection and Quantification of MicroRNAs by Ligase-Assisted Sandwich Hybridization on a Microarray. In: Microarray Technology. Methods in Molecular Biology, vol. 1368, published Nov. 27, 2015 (Year: 2015).*
International Search Report and Written Opinion for Application No. PCT/US2017/042360 dated Nov. 27, 2017.
International Preliminary Report on Patentability for Application No. PCT/US2017/042360 dated Jan. 31, 2019.

(Continued)

*Primary Examiner* — Jeremy C Flinders
(74) *Attorney, Agent, or Firm* — Wolf, Greenfield & Sacks, P.C.

(57) ABSTRACT

This disclosure demonstrates an approach that translates synthetic DNA codes to spatial codes registered in nanoliter microchambers for multiplexed measurement of nearly any type of molecular targets (e.g., miRNAs, mRNAs, intracellular and surface proteins) in single cells.

20 Claims, 13 Drawing Sheets
Specification includes a Sequence Listing.

(56) References Cited

OTHER PUBLICATIONS

Agasti et al., Photocleavable DNA barcode-antibody conjugates allow sensitive and multiplexed protein analysis in single cells. J Am Chem Soc. Nov. 14, 2012;134(45):18499-502. doi: 10.1021/ja307689w. Epub Nov. 2, 2012.

Deng et al., An integrated microfluidic chip system for single-cell secretion profiling of rare circulating tumor cells. Sci Rep. Dec. 16, 2014;4:7499. doi: 10.1038/srep07499.

Gong et al., Simple Method to Prepare Oligonucleotide-Conjugated Antibodies and Its Application in Multiplex Protein Detection in Single Cells. Bioconjug Chem. Jan. 20, 2016;27(1):217-25. doi: 10.1021/acs.bioconjchem.5b00613. Epub Jan. 4, 2016.

\* cited by examiner miR-16-5p miR-223-3p

SEQUENCE LISTING

<160> NUMBER OF SEQ ID NOS: 38

<210> SEQ ID NO 1
<211> LENGTH: 22
<212> TYPE: RNA
<213> ORGANISM: Artificial Sequence
<220> FEATURE:
<223> OTHER INFORMATION: Synthetic polynucleotide

<400> SEQUENCE: 1
ugagaacuga auccauggg uu                                           22

<210> SEQ ID NO 2
<211> LENGTH: 23
<212> TYPE: RNA
<213> ORGANISM: Artificial Sequence
<220> FEATURE:
<223> OTHER INFORMATION: Synthetic polynucleotide

<400> SEQUENCE: 2
guccaguuuu cccaggaauc ccu                                         23

<210> SEQ ID NO 3
<211> LENGTH: 22
<212> TYPE: RNA
<213> ORGANISM: Artificial Sequence
<220> FEATURE:
<223> OTHER INFORMATION: Synthetic polynucleotide

<400> SEQUENCE: 3
uagcuuauca gacugauguu ga                                          22

<210> SEQ ID NO 4
<211> LENGTH: 22
<212> TYPE: RNA
<213> ORGANISM: Artificial Sequence
<220> FEATURE:
<223> OTHER INFORMATION: Synthetic polynucleotide

<400> SEQUENCE: 4
uagcagcacg uaaauauugg cg                                          22

<210> SEQ ID NO 5
<211> LENGTH: 22
<212> TYPE: RNA
<213> ORGANISM: Artificial Sequence
<220> FEATURE:
<223> OTHER INFORMATION: Synthetic polynucleotide

<400> SEQUENCE: 5
ucucccaacc cuuguaccag ug                                          22

<210> SEQ ID NO 6
<211> LENGTH: 21
<212> TYPE: RNA
<213> ORGANISM: Artificial Sequence
<220> FEATURE:
<223> OTHER INFORMATION: Synthetic polynucleotide

<400> SEQUENCE: 6
cauaaaguag aaagcacuac u                                           21

<210> SEQ ID NO 7
<211> LENGTH: 23
<212> TYPE: RNA
<213> ORGANISM: Artificial Sequence

```
<220> FEATURE:
<223> OTHER INFORMATION: Synthetic polynucleotide

<400> SEQUENCE: 7
uuaaugcuaa ucgugauagg ggu                                             23

<210> SEQ ID NO 8
<211> LENGTH: 22
<212> TYPE: RNA
<213> ORGANISM: Artificial Sequence
<220> FEATURE:
<223> OTHER INFORMATION: Synthetic polynucleotide

<400> SEQUENCE: 8
ugucaguuug ucaauaccc ca                                               22

<210> SEQ ID NO 9
<211> LENGTH: 22
<212> TYPE: RNA
<213> ORGANISM: Artificial Sequence
<220> FEATURE:
<223> OTHER INFORMATION: Synthetic polynucleotide

<400> SEQUENCE: 9
cagcagcaau ucauguuuug aa                                              22

<210> SEQ ID NO 10
<211> LENGTH: 22
<212> TYPE: RNA
<213> ORGANISM: Artificial Sequence
<220> FEATURE:
<223> OTHER INFORMATION: Synthetic polynucleotide

<400> SEQUENCE: 10
aaggagcuca cagucuauug ag                                              22

<210> SEQ ID NO 11
<211> LENGTH: 22
<212> TYPE: RNA
<213> ORGANISM: Artificial Sequence
<220> FEATURE:
<223> OTHER INFORMATION: Synthetic polynucleotide

<400> SEQUENCE: 11
uggaguguga caauggucuu ug                                              22

<210> SEQ ID NO 12
<211> LENGTH: 23
<212> TYPE: RNA
<213> ORGANISM: Artificial Sequence
<220> FEATURE:
<223> OTHER INFORMATION: Synthetic polynucleotide

<400> SEQUENCE: 12
agcuacauug ucugcugggu uuc                                             23

<210> SEQ ID NO 13
<211> LENGTH: 79
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: Modified by 5' biotin
<220> FEATURE:
```

```
<221> NAME/KEY: misc_feature
<222> LOCATION: (39)..(40)
<223> OTHER INFORMATION: Modified by PC Linker
<220> FEATURE:
<221> NAME/KEY: misc_feature
<222> LOCATION: (79)..(79)
<223> OTHER INFORMATION: 3' inverted dT

<400> SEQUENCE: 13
aaaaaaaaaa aaatacggac ttagctccag gataaaaaaa aaaaagatat attttaaacc      60
catggaattc agttctcat                                                  79

<210> SEQ ID NO 14
<211> LENGTH: 80
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: Modified by 5' biotin
<220> FEATURE:
<221> NAME/KEY: misc_feature
<222> LOCATION: (39)..(40)
<223> OTHER INFORMATION: Modified by PC Linker
<220> FEATURE:
<221> NAME/KEY: misc_feature
<222> LOCATION: (80)..(80)
<223> OTHER INFORMATION: 3' inverted dT

<400> SEQUENCE: 14
aaaaaaaaaa aaataggcat gattcaatga ggcaaaaaaa aaaaagatat attttaaggg      60
attcctggga aaactggact                                                 80

<210> SEQ ID NO 15
<211> LENGTH: 76
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: Modified by 5' biotin
<220> FEATURE:
<221> NAME/KEY: misc_feature
<222> LOCATION: (36)..(37)
<223> OTHER INFORMATION: Modified by PC Linker
<220> FEATURE:
<221> NAME/KEY: misc_feature
<222> LOCATION: (76)..(76)
<223> OTHER INFORMATION: 3' inverted dT

<400> SEQUENCE: 15
aaaaaaaaaa aagcgatagt agacgagtgc aaaaaaaaaa aagatatatt ttatcaacat      60
cagtctgata agctat                                                     76

<210> SEQ ID NO 16
<211> LENGTH: 68
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: Modified by 5' biotin
<220> FEATURE:
<221> NAME/KEY: misc_feature
```

```
<222> LOCATION: (39)..(40)
<223> OTHER INFORMATION: Modified by PC Linker
<220> FEATURE:
<221> NAME/KEY: misc_feature
<222> LOCATION: (68)..(68)
<223> OTHER INFORMATION: 3' inverted dT

<400> SEQUENCE: 16
aaaaaaaaaa aaatactctg acatctcgac cataaaaaaa aaaaacgcca atatttacgt      60
gctgctat                                                              68

<210> SEQ ID NO 17
<211> LENGTH: 67
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: Modified by 5' biotin
<220> FEATURE:
<221> NAME/KEY: misc_feature
<222> LOCATION: (39)..(40)
<223> OTHER INFORMATION: Modified by PC Linker
<220> FEATURE:
<221> NAME/KEY: misc_feature
<222> LOCATION: (67)..(67)
<223> OTHER INFORMATION: 3' inverted dT

<400> SEQUENCE: 17
aaaaaaaaaa aaatagatac tgccacttca cataaaaaaa aaaaaactgg tacaagggtt      60
gggagat                                                               67

<210> SEQ ID NO 18
<211> LENGTH: 69
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: Modified by 5' biotin
<220> FEATURE:
<221> NAME/KEY: misc_feature
<222> LOCATION: (39)..(40)
<223> OTHER INFORMATION: Modified by PC Linker
<220> FEATURE:
<221> NAME/KEY: misc_feature
<222> LOCATION: (69)..(69)
<223> OTHER INFORMATION: 3' inverted dT

<400> SEQUENCE: 18
aaaaaaaaaa aaataccgtg aaccttacct gataaaaaaa aaaaatccat aaagtaggaa      60
acactacat                                                             69

<210> SEQ ID NO 19
<211> LENGTH: 62
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: Modified by 5' biotin
<220> FEATURE:
<221> NAME/KEY: misc_feature
<222> LOCATION: (36)..(37)
```

<223> OTHER INFORMATION: Modified by PC Linker
<220> FEATURE:
<221> NAME/KEY: misc_feature
<222> LOCATION: (62)..(62)
<223> OTHER INFORMATION: 3' inverted dT

<400> SEQUENCE: 19
aaaaaaaaaa aatgctcggg aaggctactc aaaaaaaaaa aacctatcac gattagcatt    60
at                                                                  62

<210> SEQ ID NO 20
<211> LENGTH: 68
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: Modified by 5' biotin
<220> FEATURE:
<221> NAME/KEY: misc_feature
<222> LOCATION: (39)..(40)
<223> OTHER INFORMATION: Modified by PC Linker
<220> FEATURE:
<221> NAME/KEY: misc_feature
<222> LOCATION: (68)..(68)
<223> OTHER INFORMATION: 3' inverted dT

<400> SEQUENCE: 20
aaaaaaaaaa aaacgcaccg cagtttggtc aataaaaaaa aaaaatggggg tatttgacaa    60 actgacat                                                             68

<210> SEQ ID NO 21
<211> LENGTH: 67
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: Modified by 5' biotin
<220> FEATURE:
<221> NAME/KEY: misc_feature
<222> LOCATION: (39)..(40)
<223> OTHER INFORMATION: Modified by PC Linker
<220> FEATURE:
<221> NAME/KEY: misc_feature
<222> LOCATION: (67)..(67)
<223> OTHER INFORMATION: 3' inverted dT

<400> SEQUENCE: 21
aaaaaaaaaa aaatccgacg caacaatagg gcaaaaaaaa aaaaattcaa aacatgaatt    60
gctgctt                                                              67

<210> SEQ ID NO 22
<211> LENGTH: 66
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: Modified by 5' biotin
<220> FEATURE:
<221> NAME/KEY: misc_feature
<222> LOCATION: (39)..(40)
<223> OTHER INFORMATION: Modified by PC Linker

```
<220> FEATURE:
<221> NAME/KEY: misc_feature
<222> LOCATION: (66)..(66)
<223> OTHER INFORMATION: 3' inverted dT

<400> SEQUENCE: 22
aaaaaaaaaa aaacctgctc gacaactaga agaaaaaaaa aaaaatcaat agactgtgag    60
ctcctt                                                                66

<210> SEQ ID NO 23
<211> LENGTH: 67
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: Modified by 5' biotin
<220> FEATURE:
<221> NAME/KEY: misc_feature
<222> LOCATION: (39)..(40)
<223> OTHER INFORMATION: Modified by PC Linker
<220> FEATURE:
<221> NAME/KEY: misc_feature
<222> LOCATION: (67)..(67)
<223> OTHER INFORMATION: 3' inverted dT

<400> SEQUENCE: 23
aaaaaaaaaa aaaccgcgac cagaattaga ttaaaaaaaa aaaaaaaaca ccattgtcac    60
actccat                                                               67

<210> SEQ ID NO 24
<211> LENGTH: 80
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: Modified by 5' biotin
<220> FEATURE:
<221> NAME/KEY: misc_feature
<222> LOCATION: (39)..(40)
<223> OTHER INFORMATION: Modified by PC Linker
<220> FEATURE:
<221> NAME/KEY: misc_feature
<222> LOCATION: (80)..(80)
<223> OTHER INFORMATION: 3' inverted dT

<400> SEQUENCE: 24
aaaaaaaaaa aaagccgaag cagacttaat cacaaaaaaa aaaagatat attttagaaa     60 cccagcagac aatgtagctt                                                 80

<210> SEQ ID NO 25
<211> LENGTH: 78
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: Modified by 5' biotin
<220> FEATURE:
<221> NAME/KEY: misc_feature
<222> LOCATION: (39)..(40)
<223> OTHER INFORMATION: Modified by PC Linker
<220> FEATURE:
```

```
<221> NAME/KEY: misc_feature
<222> LOCATION: (78)..(78)
<223> OTHER INFORMATION: 3' inverted dT

<400> SEQUENCE: 25
aaaaaaaaaa aaaacaggtt cagaatcctc gacaaaaaaa aaaaagatat attttaagac    60
cgctccgcca tcctgagt                                                 78

<210> SEQ ID NO 26
<211> LENGTH: 33
<212> TYPE: DNA
<213> ORGANISM: Artificial Sequence
<220> FEATURE:
<223> OTHER INFORMATION: Synthetic polynucleotide

<400> SEQUENCE: 26
aaaaaaaaaa aaaatcctgg agctaagtcc gta                                33

<210> SEQ ID NO 27
<211> LENGTH: 33
<212> TYPE: DNA
<213> ORGANISM: Artificial Sequence
<220> FEATURE:
<223> OTHER INFORMATION: Synthetic polynucleotide

<400> SEQUENCE: 27
aaaaaaaaaa aaagcctcat tgaatcatgc cta                                33

<210> SEQ ID NO 28
<211> LENGTH: 33
<212> TYPE: DNA
<213> ORGANISM: Artificial Sequence
<220> FEATURE:
<223> OTHER INFORMATION: Synthetic polynucleotide

<400> SEQUENCE: 28
aaaaaaaaaa aaagcactcg tctactatcg cta                                33

<210> SEQ ID NO 29
<211> LENGTH: 33
<212> TYPE: DNA
<213> ORGANISM: Artificial Sequence
<220> FEATURE:
<223> OTHER INFORMATION: Synthetic polynucleotide

<400> SEQUENCE: 29
aaaaaaaaaa aaaatggtcg agatgtcaga gta                                33

<210> SEQ ID NO 30
<211> LENGTH: 33
<212> TYPE: DNA
<213> ORGANISM: Artificial Sequence
<220> FEATURE:
<223> OTHER INFORMATION: Synthetic polynucleotide

<400> SEQUENCE: 30
aaaaaaaaaa aaaatgtgaa gtggcagtat cta                                33

<210> SEQ ID NO 31
<211> LENGTH: 33
<212> TYPE: DNA
<213> ORGANISM: Artificial Sequence
<220> FEATURE:
<223> OTHER INFORMATION: Synthetic polynucleotide

<400> SEQUENCE: 31
```

-continued aaaaaaaaaa aaaatcaggt aaggttcacg gta        33

<210> SEQ ID NO 32
<211> LENGTH: 30
<212> TYPE: DNA
<213> ORGANISM: Artificial Sequence
<220> FEATURE:
<223> OTHER INFORMATION: Synthetic polynucleotide

<400> SEQUENCE: 32
aaaaaaaaaa gagtagcctt cccgagcatt        30

<210> SEQ ID NO 33
<211> LENGTH: 30
<212> TYPE: DNA
<213> ORGANISM: Artificial Sequence
<220> FEATURE:
<223> OTHER INFORMATION: Synthetic polynucleotide

<400> SEQUENCE: 33
aaaaaaaaaa attgaccaaa ctgcggtgcg        30

<210> SEQ ID NO 34
<211> LENGTH: 30
<212> TYPE: DNA
<213> ORGANISM: Artificial Sequence
<220> FEATURE:
<223> OTHER INFORMATION: Synthetic polynucleotide

<400> SEQUENCE: 34
aaaaaaaaaa tgccctattg ttgcgtcgga        30

<210> SEQ ID NO 35
<211> LENGTH: 30
<212> TYPE: DNA
<213> ORGANISM: Artificial Sequence
<220> FEATURE:
<223> OTHER INFORMATION: Synthetic polynucleotide

<400> SEQUENCE: 35
aaaaaaaaaa tcttctagtt gtcgagcagg        30

<210> SEQ ID NO 36
<211> LENGTH: 30
<212> TYPE: DNA
<213> ORGANISM: Artificial Sequence
<220> FEATURE:
<223> OTHER INFORMATION: Synthetic polynucleotide

<400> SEQUENCE: 36
aaaaaaaaaa taatctaatt ctggtcgcgg        30

<210> SEQ ID NO 37
<211> LENGTH: 30
<212> TYPE: DNA
<213> ORGANISM: Artificial Sequence
<220> FEATURE:
<223> OTHER INFORMATION: Synthetic polynucleotide

<400> SEQUENCE: 37
aaaaaaaaaa gtgattaagt ctgcttcggc        30

<210> SEQ ID NO 38
<211> LENGTH: 30
<212> TYPE: DNA

```
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: Modified by Cyanine 3

<400> SEQUENCE: 38
aaaaaaaaaa gtcgaggatt ctgaacctgt                                          30
```

MULTIPLEX DETECTION OF INTRACELLULAR OR SURFACE MOLECULAR TARGETS IN SINGLE CELLS

RELATED APPLICATIONS

This application is a national stage filing under 35 U.S.C. § 371 of international patent application serial no. PCT/US2017/042360, filed Jul. 17, 2017, which claims the benefit under 35 U.S.C. § 119(e) of U.S. provisional application No. 62/363,696, filed Jul. 18, 2016, the entire contents of each of which is incorporated by reference herein in its entirety.

GOVERNMENT SUPPORT

This invention was made with government support under CA164252 and CA177393 awarded by National Institutes of Health. The government has certain rights in the invention.

REFERENCE TO A SEQUENCE LISTING SUBMITTED AS A TEXT FILE VIA EFS-WEB

This application contains a Sequence Listing which has been submitted in ASCII format via EFS-Web and is hereby incorporated by reference in its entirety. Said ASCII copy, created on Mar. 15, 2023, is named Y008770086US03-SEQ-HJD and is 11,922 bytes in size.

BACKGROUND

It has been challenging to conduct multiplex measurement of molecular targets at the single cell level. Despite the recent advances, mass cytometry requires sophisticated and costly analysis. In particular, it is difficult to perform mass cytometry if the sample size is limited (e.g., a few thousand cells). Mass cytometry is also limited to the detection of protein targets. To date, there is no technology that can detect multiple types of molecular targets in a highly multiplexed manner and in single cells.

SUMMARY

This disclosure provides methods, systems, kits, devices and compositions that can be used for multiplex detection of proteins and/or nucleic acid (e.g., RNA or DNA) targets (e.g., intracellular targets). This technology can be used to translate synthetic nucleic acid (e.g., DNA) codes to spatial and spectral codes registered in nanoliter microchambers for multiplexed measurement of many types of molecular targets (e.g., miRNAs, mRNAs, intracellular and surface proteins) in single cells, for example. Both the spatial location and spectral properties of the detectable reporter constructs of the present disclosure correlate to a particular molecular target of interest and to a particular single cell. Thus, this technology provides an efficient and cost-effective means for single cell, high throughput, multiplex detection of proteins and/or nucleic acids in the fields of systems biology, cell signaling, and genomics, as well as for the development of therapeutics for inhibiting or activating signaling pathways or gene expression, for example.

As a non-limiting example, the technology provided herein may be used for high-throughput, multiplex detection of microRNA (miRNA) biomarkers in single cells. miRNAs are a class of small non-coding RNAs, often functioning as negative gene regulators. Many miRNAs are located within fragile regions of chromosomes, which are areas of the genome more tightly associated with human cancers, indicating the possible role of miRNAs in tumor development. miRNA expression profiles correlate with various cancers and the miRNA signatures are potentially unique cancer biomarkers to accurately diagnose and classify human cancers. Human cancers, however, are highly heterogeneous due in part to the high degree of intratumoral heterogeneity at the single-cell level. Thus, characterizing these human cancers can require evaluating a large number of single tumor cells, each having its own miRNA expression profile. The methods, systems, kits, devices and compositions, as provided herein, enable high-throughput and multiplex miRNA detection in single cells, without the length process of amplification. More specifically, this technology, in some embodiments, integrates a barcoded nucleic acid arrays and molecular conjugates with a nanoliter microfluidics platform (e.g., chip) to enable multiplexed detection of many (e.g., at least 5, 10, 12, 15, 20, 30, 40 or 50) miRNA biomarkers (or other intracellular biomarkers) from a large number of single cancer cells. This technology is not only a versatile platform for detecting miRNA biomarkers implicated in a variety of human cancers, but it can also be used to detect other non-encoding RNAs and messenger RNA biomarkers from single cells.

Thus, the present disclosure provides methods comprising (a) contacting cells that comprise nucleic acid targets with at least two (e.g., at least 3, at least 4, at least 5, at least 10, at least 20, or at least 50) conjugates, each conjugate comprising (i) a nucleic acid bait strand linked to (ii) a nucleic acid reporter strand through (iii) a cleavable linker, wherein the nucleic acid bait strand contains a nucleotide sequence complementary to a nucleic acid target of interest, to produce modified cells comprising target-conjugate complexes, and (b) loading modified cells of step (a) on a base substrate (e.g., microchip) containing microwells (or other means of containing a small volume of cells in solution), to produce a loaded base substrate.

Also provided herein are methods comprising (a) contacting cells that comprise protein targets with at least two (e.g., at least 3, at least 4, at least 5, at least 10, at least 20, or at least 50) conjugates, each conjugate comprising (i) an antibody linked to (ii) a nucleic acid reporter strand through (iii) a cleavable linker, wherein the antibody binds specifically to a protein target of interest, to produce modified cells comprising target-conjugate complexes, and (b) loading modified cells of step (a) on a base substrate (e.g., microchip) containing microwells (or other means of containing a small volume of cells in solution), to produce a loaded base substrate.

In some embodiments, the methods further comprise (c) contacting the loaded base substrate with a cover substrate (e.g., glass cover) comprising at least two (e.g., at least 3, at least 4, at least 5, or at least 10) sets of at least two (e.g., at least 3, at least 4, at least 5, or at least 10) immobilized (e.g., fixed to the cover substrate) nucleic acid capture probes, each capture probe comprising a nucleotide sequence complementary to a nucleotide sequence of a nucleic acid reporter strand of step (a), to produce at least two enclosed (e.g., sealed) microwells, each of the at least two enclosed microwells containing a (e.g. a single) set of at least two (e.g., at least 3, at least 4, at least 5, or at least 10) different capture probes (e.g., unique relative to each other with a set) of the cover substrate.

In some embodiments, the methods further comprise (d) cleaving the cleavable linkers of the conjugates to release the nucleic acid reporter strands. This cleaving step may be performed before or after the cover substrate is contacted with (applied to) the base substrate.

In some embodiments, the methods further comprise maintaining the enclosed (e.g., sealed) microwells under nucleic acid hybridization conditions to produce reporter-capture complexes immobilized on the cover substrate. Nucleic acid hybridization conditions may be determined, for example, based on the length and sequence of nucleic acids intended to hybridize together (bind to each other).

In some embodiments, the methods further comprise dissociating (detaching, removing) the cover substrate containing the immobilized reporter-capture complexes from the base substrate and visualizing at least one reporter-capture complex immobilized on the cover substrate. The reporters, in some embodiments, are linked to a fluorescent molecule such as a fluorophore that can be detected under a fluorescent microscope.

In some embodiments, the methods further comprise identifying at least one nucleic acid target of interest of (a). The location and spectral properties of the immobilized reporter correlate to a particular target of interest as well as the cell from which the target was obtained.

In some embodiments, step (a) comprises contacting cells that comprise nucleic acid targets with at least 3, at least 4, at least 5, at least 10, at least 15, at least 20, at least 25, at least 30, at least 35, at least 40, at least 45, or at least 50 conjugates.

In some embodiments, the cells are permeabilized (e.g., mechanically, chemically, or enzymatically) and/or fixed (e.g., in paraformaldehyde, methanol, or acetone).

In some embodiments, the nucleic acid bait strand contains a nucleotide sequence complementary to a ribonucleic acid (RNA) target. For example, the RNA target may be selected from mRNA targets (messenger RNA), tRNA (transfer RNA) targets, rRNA (ribosomal RNA) targets and miRNA (micro RNA) targets.

In some embodiments, the nucleic acid bait strand contains a nucleotide sequence complementary to a deoxyribonucleic acid (DNA) target (e.g., gene or gene fragment).

In some embodiments, the antibody is a monoclonal antibody. In some embodiments, the antibody is a monoclonal antibody. In some embodiments, the antibody is a humanized antibody. In some embodiments, the antibody is a chimeric antibody.

In some embodiments, the cleavable linker is selected from photocleavable linkers and enzyme-cleavable linkers.

In some embodiments, the nucleic acid reporter strand is linked to a detectable label. The detectable label may be, for example, a fluorescent label (e.g., a fluorophore).

In some embodiments, the base substrate is a microchip, microplate, microwell plate, multiwall plate, or a MICROTITER® plate. A microwell is a structure capable of containing microliter volumes of solution or particulate (e.g., cells). The foregoing terms and substrates are well known in the art.

In some embodiments, the base substrate contains 2-20,000 microwells. For example, the base substrate may contain 5,000-20,000 microwells.

In some embodiments, each microwell has a volume of 1-999 nanoliters. For example, each microwell may have a volume of 1-10 nanoliters.

In some embodiments, step (b) comprises loading modified cells formulated in a suspension (e.g., liquid buffer) having a volume of 1-10 nanoliters.

In some embodiments, the base substrate is comprised of polydimethylsiloxane (PDMS) or glass.

In some embodiments, the cover substrate is comprised of PDMS or glass.

In some embodiments, the cover substrate forms a seal with the base substrate to prevent fluid communication among the enclosed microwells.

The present disclosure also provides, in some embodiments, devices comprising (a) a base substrate comprising microwells, each microwell containing at least one cell (e.g., at least 2, 3, 4 or 5 cells; or less than 5 cells) containing at least two (e.g., 2-50) target-conjugate complexes, each complex comprising a nucleic acid target bound to a nucleic acid bait strand linked to a nucleic acid reporter strand through a cleavable linker, and (b) a cover substrate comprising at least two sets (e.g., at least 3, at least 4, at least 5, or at least 10) of at least two (e.g., at least 3, at least 4, at least 5, or at least 10) immobilized nucleic acid capture probes, each capture probe comprising a nucleotide sequence complementary to a nucleotide sequence of a nucleic acid reporter strand of (a), wherein the cover substrate is in contact with the base substrate to form at least two (e.g., 2-20,000) enclosed microwells, each of the at least two enclosed microwells containing a (e.g., a single) set of at least two capture probes of the cover substrate.

The present disclosure also provides, in some embodiments, devices comprising (a) a base substrate comprising microwells, each microwell containing at least one (e.g., at least 2, 3, 4 or 5 cells; or less than 5 cells) cell containing at least two (e.g., 2-50) target-conjugate complexes, each complex comprising a protein target bound to an antibody linked to a nucleic acid reporter strand through a cleavable linker, and (b) a cover substrate comprising at least two sets (e.g., at least 3, at least 4, at least 5, or at least 10) of at least two (e.g., at least 3, at least 4, at least 5, or at least 10) immobilized nucleic acid capture probes, each capture probe comprising a nucleotide sequence complementary to a nucleotide sequence of a nucleic acid reporter strand of (a), wherein the cover substrate is in contact with the base substrate to form at least two enclosed microwells, each of the at least two (e.g., 2-20,000) enclosed microwells containing a set of at least two capture probes of the cover substrate.

DETAILED DESCRIPTION

Figure 1:
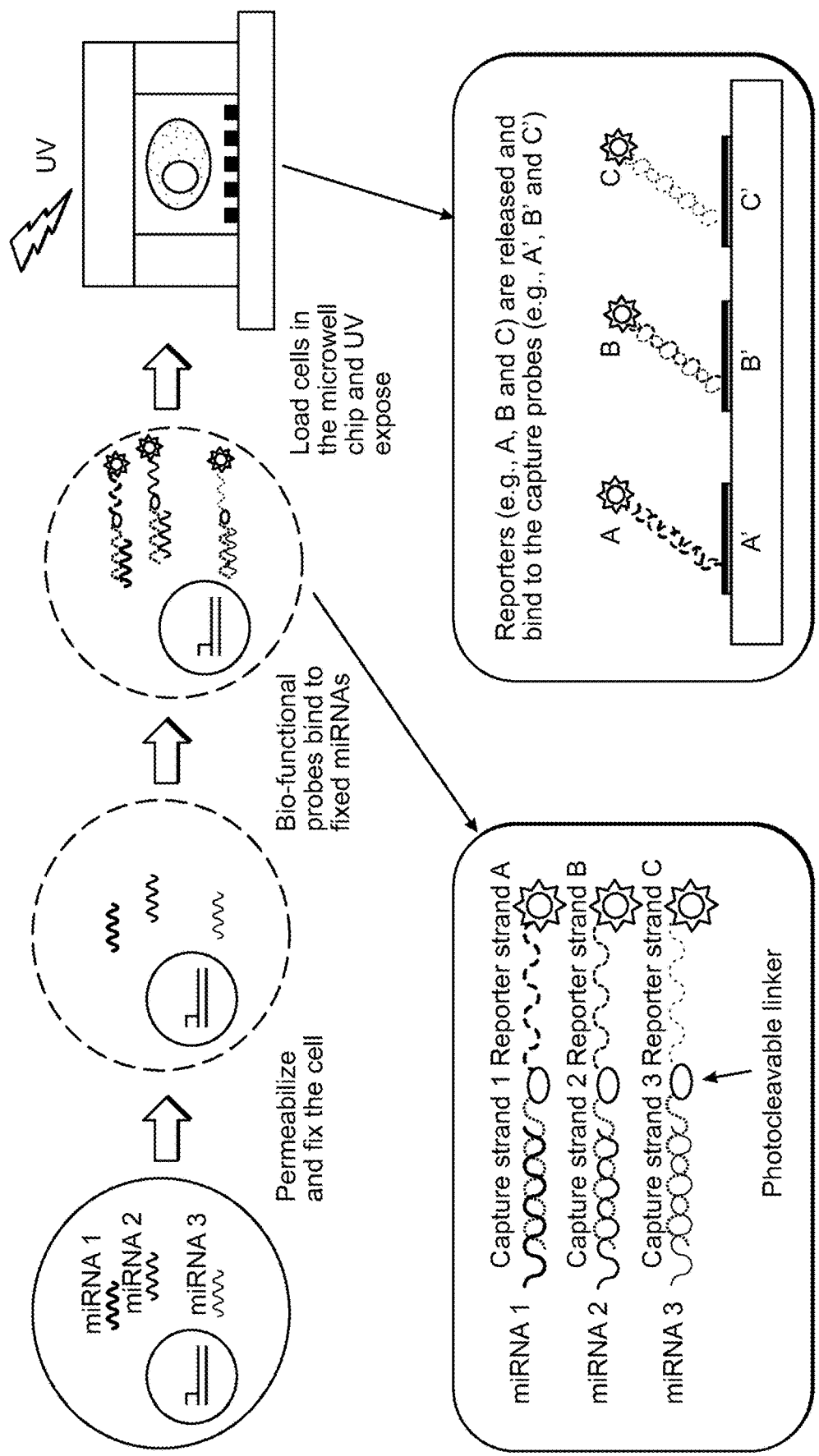
FIG. 1 is a schematic representation of some embodiments of a method for multiplex detection of intracellular targets from an individual cell.
Figure 2:
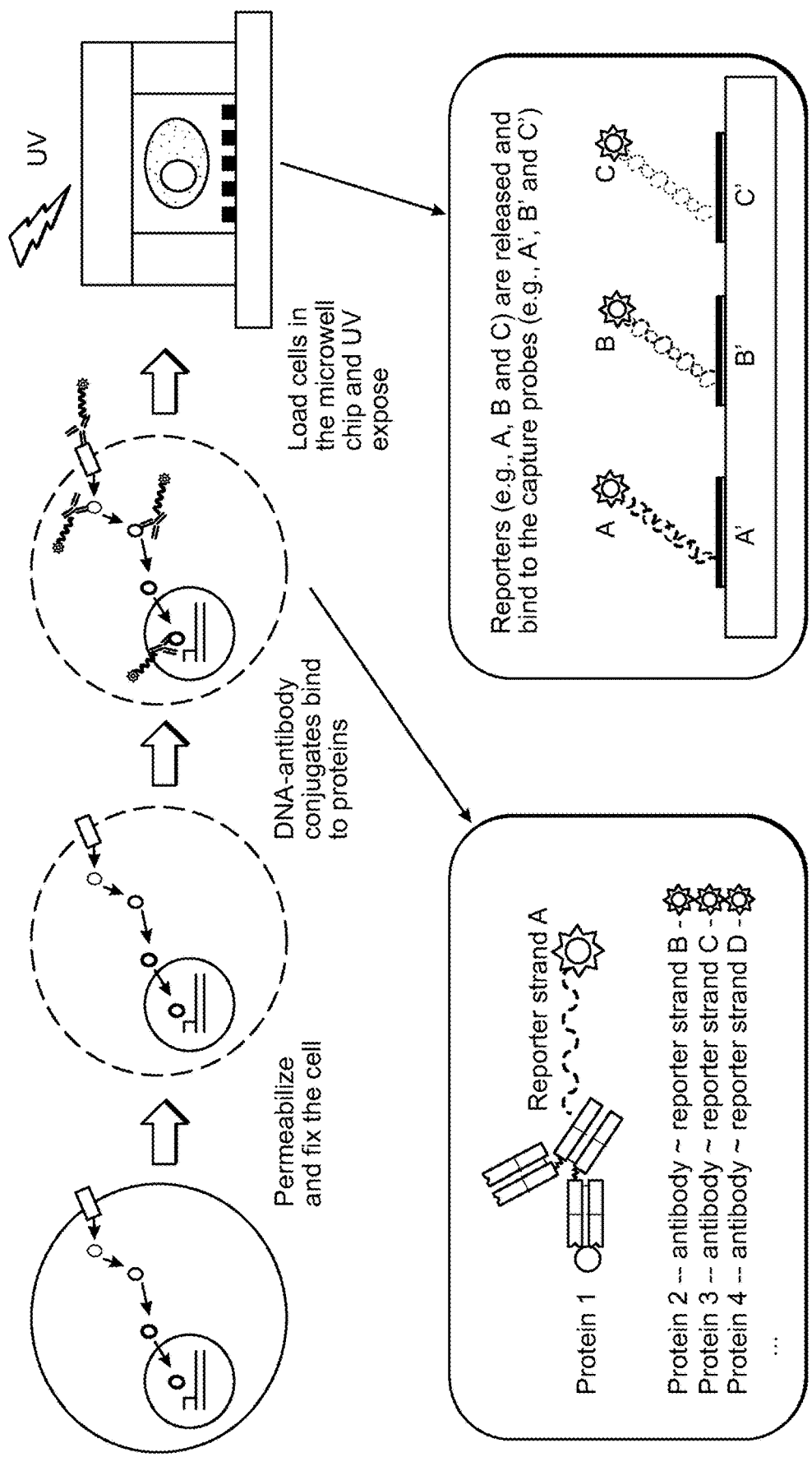
FIG. 2 is a schematic representation of some embodiments of a method for multiplex detection of intracellular targets from an individual cell.

The present disclosure provides, in some embodiments, methods comprising (a) contacting cells comprising nucleic acid and/or protein (or peptide) targets with reporter-probe conjugates ("RPC" or "conjugates"), each conjugate comprising (i) a nucleic acid bait strand or an antibody linked to (ii) a nucleic acid reporter strand through (iii) a cleavable linker, wherein the nucleic acid bait strand contains a nucleotide sequence complementary to a nucleic acid target of the cells or wherein the antibody binds specifically to the protein (or peptide) target of interest, to produce modified cells comprising target-conjugate complexes, and (b) loading modified cells of step (a) on a base substrate containing microwells, to produce a loaded base substrate (see, e.g., FIGS. 1 and 2).

Also provided herein are devices comprising (a) a base substrate comprising microwells, each microwell containing at least one cell containing at least two target-conjugate complexes, each complex comprising a nucleic acid or protein target bound to a nucleic acid bait strand linked to a nucleic acid reporter strand through a cleavable linker; and (b) a cover substrate comprising at least two sets of at least two immobilized capture probes, each capture probe comprising a nucleotide sequence complementary to a nucleotide sequence of a nucleic acid reporter strand of (a), wherein the cover substrate is in contact with the base substrate to form at least two enclosed microwells, each of the at least two enclosed microwells containing a set of at least two capture probes of the cover substrate.

The cells used as provided herein may be prokaryotic cells (e.g., bacterial cells such as *Escherichia coli* cells) or eukaryotic cells (e.g., mammalian or yeast cells). In some embodiments, the cells are mammalian cells. For example, the cells may be human cells. In some embodiments, the cells are tumor cells. The tumor cells may be non-cancerous or cancerous. Thus, in some embodiments, the cells are cancer cells. Modified cells are cells containing exogenous (not native) protein or nucleic acid.

In some embodiments, the cells are fixed and/or permeabilized prior to contacting the cells with the conjugates. Methods of fixation and permeabilization are known, any of which may be used as provided herein. In some embodiments, the cells are not fixed. In some embodiments, the cells are not permeabilized.

Nucleic acid targets are typically intracellular targets. In some embodiments, the nucleic acid targets are RNA targets (e.g., mRNA, tRNA, rRNA and/or miRNA). In some embodiments, the nucleic acid targets are DNA targets. Targets may be a combination of RNA targets and DNA targets.

Protein (or peptide) targets may be intracellular proteins or cell surface proteins (e.g., receptors). A protein target is not limited by type. For example, a protein may be an enzyme, hormone, receptor, ligand, or other type of protein.

In some embodiments, the nucleic acid target and/or the protein target is a biomarker, indicative of a disease or condition, for example cancer.

Depending in part on the number of targets of interest, cells may be contacted with at least two conjugates. In some embodiments, cells are contacted with at least 3, 4, 5, 6, 7, 8, 9 or 10 conjugates. In some embodiments, cells are contacted with 2-5, 2-10, 2-15, 5-10, 5-15, 3-5, 3-10 or 3-15 conjugates. More than 10 conjugates may be used. For example, at least 10, 15, 20, 25, 30, 35, 40, 45 or 50 (e.g., 2-10 or 2-50) conjugates may be used.

A conjugate (or RPC) as provided herein includes a nucleic acid (e.g., DNA) bait strand linked to a nucleic acid (e.g., DNA) reporter strand through a cleavable linker. In some embodiments, a nucleic acid bait strand and/or a nucleic acid reporter strand has a length of 4-50 nucleotides. For example, a nucleic acid bait strand and/or a nucleic acid reporter strand may have a length of 4, 5, 10, 15, 20, 25, 30, 35, 40, 45 or 50 nucleotides. In some embodiments, a nucleic acid bait strand and/or a nucleic acid reporter strand has a length longer than 50 nucleotides.

The cleavable linker may be, for example, a photocleavable linker (e.g., nitrobenzyl linker), disulfide bridge and/or phosphate linkage. Many different cleavable linkers are known, any of which may be used as provided herein.

Nucleic acid bait strands include a nucleotide sequence that is complementary to a nucleotide sequence of a target nucleic acid. Thus, under conditions that permit nucleic acid hybridization, the nucleic acid bait strand is able to bind (hybridize) to the target nucleic acid and/or the nucleic acid reporter strand is able to bind (hybridize) to the nucleic acid capture probe. The complementarity between nucleic acid strands intended for hybridization need not be, but in some embodiments is, wholly (100%) complementary. In some embodiments, a nucleic acid bait strand is only partially complementary (e.g., at least 50, 60, 70, 70 to 90% complementary) to a nucleic acid target strand. In some embodiments, a nucleic acid reporter strand is only partially complementary (e.g., at least 50, 60, 70, 70 to 90% complementary) to a nucleic acid capture probe.

Nucleic acid reporter strands include a detectable label, such as a fluorophore. For example, a nucleic acid reporter strand may be labeled with Hydroxycoumarin, Aminocoumarin, Methoxycoumarin, Cascade Blue, Pacific Blue, Pacific Orange, Lucifer yellow, NBD, R-Phycoerythrin (PE), PE-Cy5 conjugates, PE-Cy7 conjugates, Red 613, PerCP, TruRed, FluorX, Fluorescein, BODIPY-FL, Cy2, Cy3, Cy3B, Cy3.5, Cy5, Cy5.5, Cy7, TRITC, X-Rhodamine, Lissamine Rhodamine B, Texas Red, Allophycocyanin (APC), and/or APC-Cy7 conjugates. Other dyes and fluorescent labels are encompassed herein.

Binding of the nucleic acid bait strand to a target produces a target-conjugate complex, which is then subject to cleavage conditions (cleaved) such that the nucleic acid reporter strand of the conjugate is released from the nucleic acid bait strand and, thus, released from the target-conjugate complex. The free nucleic acid reporter strand can then bind to an immobilized capture probe.

Modified cells containing the target-conjugate complexes are loaded onto (delivered to) a base substrate containing microwells to produce a loaded base substrate. The base substrate may be comprised of glass or plastic (or other material), for example. In some embodiments a base substrate is a microchip (e.g., similar to a microarray) or a microplate.

In some embodiments, a single microwell contains a single cell, although more cells may be contained within a single microwell. In some embodiments, a single microwell comprises 1, 2, 3, 4, 5, 6, 7, 8, 9 or 10 cells. In some embodiments, a single microwell comprises 1-2, 1-3, 1-4, 1-5, 1-6, 1-7, 1-8, 1-9 or 1-10 cells. In some embodiments, a single microwell comprises 5 cells or less, or less than 5 cells. In some embodiments, 25-33% of the microwells of a base substrate contain only a single cell. In some embodiments, at least 30% of the microwells of a base substrate contain only a single cell. For example, at least 35%, 40%, 45%, 50%, 55%, 60%, 65%, 70%, 75%, 80%, 85%, 90%, 95% or 98% of the microwells of a base substrate contain only a single cell. In some embodiments, all (100%) of the microwells of a base substrate contain only a single cell.

A base substrate may include any number of microwells. For example, a base substrate (e.g., microchip or microplate) may include 2-10, 2-20, 2-50, 2-100, 2-500, 2-1000, 2-5000, 2-10000, or 2-20000 microwells.

Each microwell may have a volume of 1 nanoliter to 999 nanoliters, for example. In some embodiments, a microwell has a volume of 1, 5, 10, 20, 30, 40, 50, 60, 70, 80, 90, 100, 200, 300, 400, 500, 600, 700, 800, or 900 nanoliters. In some embodiments, a microwell has a volume of 1-10, 1-15 or 1-20 nanoliters.

In some embodiments, cells are loaded into the microwells as a suspension (e.g., in buffer, such as saline buffer) having a volume of 1-10 nanoliters.

Following loading of cells into the microwells, the loaded microwells (loaded base substrate) are contacted with a cover substrate comprising at least 2 sets of at least 2 immobilized capture probes. In some embodiments, the loaded microwells (loaded base substrate) are contacted with a cover substrate comprising at least 2 sets of at least 3 immobilized capture probes. In some embodiments, the loaded microwells (loaded base substrate) are contacted with a cover substrate comprising at least 3 sets of at least 2 immobilized capture probes. In some embodiments, the loaded microwells (loaded base substrate) are contacted with a cover substrate comprising at least 3 sets of at least 3 immobilized capture probes. In some embodiments, the loaded microwells (loaded base substrate) are contacted with a cover substrate comprising at least 4 sets of at least 2 immobilized capture probes. In some embodiments, the loaded microwells (loaded base substrate) are contacted with a cover substrate comprising at least 4 sets of at least 3 immobilized capture probes. In some embodiments, the loaded microwells (loaded base substrate) are contacted with a cover substrate comprising at least 4 sets of at least 4 immobilized capture probes. In some embodiments, the loaded microwells (loaded base substrate) are contacted with a cover substrate comprising at least 5 sets of at least 2 immobilized capture probes. In some embodiments, the loaded microwells (loaded base substrate) are contacted with a cover substrate comprising at least 5 sets of at least 3 immobilized capture probes. In some embodiments, the loaded microwells (loaded base substrate) are contacted with a cover substrate comprising at least 5 sets of at least 4 immobilized capture probes. In some embodiments, the loaded microwells (loaded base substrate) are contacted with a cover substrate comprising at least 5 sets of at least 5 immobilized capture probes.

The cover substrate may be glass or plastic, for example. It may be a flat substrate such that it encloses and seals the microwells of the base substrate, thus preventing fluid communication among the enclosed microwells.

Capture probes comprise a nucleotide sequence complementary to a nucleotide sequence of a nucleic acid reporter strand (of a conjugate). Released reporter strands (following cleavage) bind to nucleic acid capture probes. The capture probes are typically provided as multiple sets of probes immobilized and patterned (e.g., arrayed in parallel) on a cover substrate. For example, a single set of capture probes may include 3, 4, 5 or more different capture probes, each probe coded for (capable of binding to) a different reporter strand (corresponding to a different cellular target). A cover substrate includes multiple sets of capture probes patterned such that any single microwell contains a (at least one)

complete set of capture probes, when the cover substrate is placed into contact with the base substrate. As an example, a single set of capture probes may include capture probe A', capture probe B' and capture probe C'. The cover substrate contains multiple immobilized sets of capture probe A', capture probe B' and capture probe C' positioned (e.g., in linear, parallel form—see, e.g., FIG. 7) to mirror the position of the microwells of the base substrate such that each microwell when enclosed by the cover substrate is exposed to (contains) a complete immobilized capture set containing capture probe A', capture probe B' and capture probe C'. Thus, each cell (or multiple cells) of a microwell is exposed to a complete set of capture probes.

A single set of capture probes may comprise at least 2, 3, 4, 5, 6, 7, 8, 9 or 10 different capture probes. In some embodiments, a single set of capture probes comprises 2-5, 2-10, 2-15, 5-10, 5-15, 3-5, 3-10 or 3-15 capture probes. More than 10 capture probes may be used. For example, at least 10, 15, 20, 25, 30, 35, 40, 45 or 50 capture probes may be used.

A cover substrate may comprises at least 2, 3, 4, 5, 6, 7, 8, 9, 10, 20, 30, 40, or 50 sets of capture probes (e.g., 2-50 captures probes per set). In some embodiments, a cover substrate comprises 2-10, 2-20, 2-50, 2-100, 2-500, 2-1000, 2-5000, 2-10000, or 2-20000 sets of capture probes.

In some embodiments, the methods further comprise cleaving the cleavable linkers of the conjugates to release the nucleic acid reporter strands. Cleavage conditions typically depend on the type of cleavable linker used. Examples of cleavable linkers are known and provided elsewhere herein.

In some embodiments, the methods further comprise maintaining enclosed microwells under nucleic acid hybridization conditions to produce reporter-capture complexes immobilized on the cover substrate. Conditions that permit complementary nucleic acids to bind (hybridize) to each other are known and/or determined based in part on the length and composition of the nucleic acids (e.g., low stringency or high stringency, low salt, particular buffers, times and temperatures).

In some embodiments, the methods further comprise dissociating (removing) the cover substrate containing the immobilized reporter-capture complexes from the base substrate and visualizing at least one reporter-capture complex immobilized on the cover substrate.

In some embodiments, the methods further comprise identifying at least one nucleic acid target of interest of (a). Targets are identified based a correlation between the target identity and the spatial location and spectral property of a corresponding immobilized reporter strand.

The present disclosure, in some embodiments, is related to methods of multiplexed detection of cell surface and/or intracellular targets on or in a single cell or a pool of individual cells. The present method also relates to detecting more than one cell surface target and/or intracellular target, on or in a single cell or a pool of individual cells. In some embodiments, the method of multiplexed detecting of more than one cell surface target on an individual cell comprises: (a) incubating cells with at least two reporter-probe conjugates (RPC), each of which comprises, in the following order: (1) an antibody that binds a cell surface target; (2) a cleavable linker; and (3) a nucleic acid reporter molecule of known sequence, under conditions under which antibody components of the RPCs bind to their cell surface targets, thereby producing cells to which RPCs are bound to a target on their surface; (b) washing the product of (a) to remove unbound RPCs and produce a suspension of cells that bear (have bound to their surface) a RPC; (c) loading the suspension produced in (b) onto a microchip comprising nanoliter microwells and producing a microchip comprising nanoliter microwells that contain a single cell; (d) covering the microchip produced in (c) with a substrate bearing a microarray comprising nucleic acid probes complementary to the nucleic acid reporter molecules of (a)(3) and arrayed in a known spatial arrangement; (e) identifying microwells of (d) that contain a single cell; (f) maintaining the microwells that contain a single cell under conditions under which the cleavable linkers of the surface target-bound RPCs in the microwells are cleaved and the reporter molecules are released from the cells to which RPCs are bound to a target on their surface, and the released reporter molecules hybridize to complementary nucleic acid probes on the microarray and produce reporter molecule nucleic acid-nucleic acid probe complexes bound to the substrate; (g) removing the substrate bearing the complexes produced in (f) from the microchip; and (h) detecting whether nucleic acid-nucleic acid probe complexes are bound to the substrate, and if complexes are bound, determining that cell surface targets are present on the cell. In some embodiments, the identity of the intracellular target is determined with reference to the position of the complementary nucleic acid on the microarray, which specifies the target identity. For example, the combination of surface antigens CD3 and CD8 can define the cytotoxic T lymphocytes. Surface antigens such as CD3, CD4, CD8, CD11a, CD11b, CD12 and CD24 can be measured together to distinguish different immune cell phenotypes.

In some embodiments, the method of multiplexed detecting of more than one cell surface target on each member of a pool of individual cells comprises: (a) incubating the cells with at least two reporter-probe conjugates (RPC) each of which comprises, in the following order: (1) an antibody that binds a cell surface target; (2) a cleavable linker; and (3) a nucleic acid reporter molecule of known sequence, under conditions under which antibody components of the RPCs bind to their cell surface targets, thereby producing cells to which RPCs are bound to a target on their surface; (b) washing the product of (a) to remove unbound RPCs and produce a suspension of cells that bear (have bound to their surface) a RPC; (c) loading the suspension produced in (b) onto a microchip comprising nanoliter microwells and producing a microchip comprising nanoliter microwells that each contain a pool of individual cells; (d) covering the microchip produced in (c) with a substrate bearing a microarray comprising nucleic acid probes complementary to the nucleic acid reporter molecules of (a)(3) and arrayed in a known spatial arrangement; (e) identifying microwells of (d) that contain a pool of individual cells; (f) maintaining the microwells that each contain a pool of individual cells under conditions under which the cleavable linkers of the surface target-bound RPCs in the microwells are cleaved and the reporter molecules are released from each member of the pool of individual cells to which RPCs are bound to a target on their surface, and the released reporter molecules hybridize to complementary nucleic acid probes on the microarray and produce reporter molecule nucleic acid-nucleic acid probe complexes bound to the substrate; (g) removing the substrate bearing the complexes produced in (f) from the microchip; and (h) detecting whether nucleic acid-nucleic acid probe complexes are bound to the substrate, and if complexes are bound, determining that cell surface targets are present on members of the pool of individual cells. In some embodiments, the identity of the intracellular target is determined with reference to the position of the complementary nucleic acid on the microarray, which specifies the target identity. In some embodiments, the pool of cells comprises a single cell type. In some embodiments, the pool of cells comprises multiple cell types.

In some embodiments, the method of multiplexed detecting of more than one intracellular target in an individual cell comprises: (a) producing a suspension of fixed, permeabilized cells; (b) incubating cells of (a) with at least two reporter-probe conjugates (RPC) each of which comprises, in the following order: (1) a nucleic acid bait that hybridizes to an intracellular target; (2) a cleavable linker; and (3) a nucleic acid reporter molecule of known sequence, under conditions under which nucleic acid bait components of the RPCs bind to their intracellular targets, thereby producing cells comprising intracellular target-bound RPCs; (c) washing the product of (b) to remove unbound RPCs and produce a suspension of cells that bear (have bound to intracellular targets) a RPC; (d) loading the suspension produced in (c) onto a microchip comprising nanoliter microwells and producing a microchip comprising nanoliter microwells that contain a single cell; (e) covering the microchip produced in (d) with a substrate bearing a microarray comprising nucleic acid probes complementary to the nucleic acid reporter molecules of (b)(3) and arrayed in a known spatial arrangement; (f) identifying microwells of (e) containing a single cell; (g) maintaining the microwells that contain a single cell under conditions under which the cleavable linkers of the intracellular target-bound RPCs in the microwells are cleaved and the reporter molecules are released from the cells to which RPCs are bound to an intracellular target, and the released reporter molecules hybridize to complementary nucleic acid probes on the microarray and produce reporter molecule nucleic acid-nucleic acid probe complexes bound to the substrate; (h) removing the substrate bearing the complexes produced in (g) from the microchip; and (i) determining whether nucleic acid-nucleic acid probe complexes are bound to the substrate, and if complexes are bound, determining that cell surface targets are present on the cell. In some embodiments, the identity of the intracellular target is determined with reference to the position of the complementary nucleic acid on the microarray, which specifies the target identity. For example, the detection of intracellular proteins such as p-Akt can determine the proliferation potential of a give type of cancer cells. Detecting a panel of intracellular proteins such as pEGFR, pERK and pS6 can distinguish the differential roles of Ras and Pi3K-Akt pathways in determining the fate of individual cells including a heterogeneous population of cancer cells.

In some embodiments, the method of multiplexed detecting of more than one intracellular target on each member of a pool of individual cells comprises: (a) producing a suspension of fixed, permeabilized cells; (b) incubating cells of (a) with at least two reporter-probe conjugates (RPC) each of which comprises, in the following order: (1) a nucleic acid bait that hybridizes to an intracellular target; (2) a cleavable linker; and (3) a nucleic acid reporter molecule of known sequence, under conditions under which nucleic acid bait components of the RPCs bind to their intracellular targets, thereby producing cells comprising intracellular target-bound RPCs; (c) washing the product of (b) to remove unbound RPCs and produce a suspension of cells that bear (have bound to intracellular targets) a RPC; (d) loading the suspension produced in (c) onto a microchip comprising nanoliter microwells and producing a microchip comprising nanoliter microwells that each contain a pool of individual cells; (e) covering the microchip produced in (d) with a substrate bearing a microarray comprising nucleic acid probes complementary to the nucleic acid reporter molecules of (b)(3) and arrayed in a known spatial arrangement; (f) identifying microwells of (e) that each contain a pool of individual cells; (g) maintaining the microwells that contain a single cell under conditions under which the cleavable linkers of the intracellular target-bound RPCs in the microwells are cleaved and the reporter molecules are released from each member of the pool of individual cells to which RPCs are bound to an intracellular target, and the released reporter molecules hybridize to complementary nucleic acid probes on the microarray and produce reporter molecule nucleic acid-nucleic acid probe complexes bound to the substrate; (h) removing the substrate bearing the complexes produced in (g) from the microchip; and (i) detecting whether nucleic acid-nucleic acid probe complexes are bound to the substrate, and if complexes are bound, determining that intracellular targets are present inside members of the pool of individual cells. In some embodiments, the identity of the intracellular target is determined with reference to the position of the complementary nucleic acid on the microarray, which specifies the target identity. In some embodiments, the pool of cells comprises a single cell type. In some embodiments, the pool of cells comprises multiple cell types. For example, the detection of intracellular proteins such as p-Akt can determine the proliferation potential of a give type of cancer cells. Detecting a panel of intracellular proteins such as pEGFR, pERK and pS6 can distinguish the differential roles of Ras and Pi3K-Akt pathways in determining the fate of individual cells including a heterogeneous population of cancer cells.

In some embodiments, the method of multiplexed detecting more than one of low abundance cell surface targets of an individual cell comprises: (a) incubating cells with at least two reporter-probe conjugates (RPC) each of which comprises, in the following order: (1) an antibody that binds to a low abundance cell surface target; (2) a cleavable linker; and (3) a nucleic acid reporter molecule of known sequence, under conditions under which antibody components of the RPCs bind to their cell surface targets, thereby producing cells to which RPCs are bound to a target on their surface; (b) washing the product of (a) to remove unbound RPCs and produce a suspension of cells that bear (have bound to their surface) a RPC; (c) loading (1) the suspension produced in (b); and (2) PCR enzymes and PCR oligonucleotide primers complementary to the nucleic acid reporter molecule of (b)(3) onto a microchip comprising nanoliter microwells, thereby producing a microchip comprising nanoliter microwells that contain a single cell and PCR enzymes and oligonucleotide primers; (d) covering the microchip produced in (c) with a substrate comprising a hydrophobic surface, under conditions under which the hydrophobic surface contacts the microwells of (c); (e) maintaining the microwells that contain a single cell and PCR enzymes and PCR oligonucleotides under conditions under which the cleavable linkers of the surface target-bound RPCs in the microwells are cleaved and the reporter molecules are released from the cells to which RPCs are bound to a target on their surface; (f) amplifying the cleaved nucleic acid reporter molecules of (e) by PCR, thereby producing a plurality of amplification products in each microwell; (g) lowering the temperature inside the microwells of (f) and providing conditions under which the amplification products of (f) do not interact with the substrate of (d); (h) maintaining the conditions of (g) and removing the substrate of (d) from the microchip; (i) covering the microchip produced in (h) with a substrate bearing a microarray comprising nucleic acid probes complementary to the amplification products of (f) and arrayed in a known spatial arrangement; (j) combining the amplification products of (f) with the nucleic acid probes complementary to the amplification products under conditions under which the amplification products and the nucleic acid probes hybridize on the microarray of the substrate and produce amplification product-nucleic acid probe complexes bound to the substrate; (k) identifying microwells of (f) containing a single cell; (l) removing the substrate bearing the complexes produced in (j) from the microchip; and (m) detecting whether nucleic acid-nucleic acid probe complexes are bound to the substrate, and if complexes are bound determining that cell surface targets are present on the cell. In some embodiments, the identity of the intracellular target is determined with reference to the position of the complementary nucleic acid on the microarray, which specifies the target identity. For example, surface antigen PD-1, which is immune check point protein, has a very wide range of expression levels. The ability to detect low abundance expression of PD-1 is of significance in determining the activation state of individual immune cells.

In some embodiments, the method of multiplexed detecting of more than one low abundance cell surface target on each member of a pool of cells comprises: (a) incubating cells with at least two reporter-probe conjugates (RPC) each of which comprises, in the following order: (1) an antibody that binds to a low abundance cell surface target; (2) a cleavable linker; and (3) a nucleic acid reporter molecule of known sequence, under conditions under which antibody components of the RPCs bind to their cell surface targets, thereby producing cells to which RPCs are bound to a target on their surface; (b) washing the product of (a) to remove unbound RPCs and produce a suspension of cells that bear (have bound to their surface) a RPC; (c) loading (1) the suspension produced in (b); and (2) PCR enzymes and PCR oligonucleotide primers complementary to the nucleic acid reporter molecule of (b)(3) onto a microchip comprising nanoliter microwells, thereby producing a microchip comprising nanoliter microwells that each contain a pool of individual cells and PCR enzymes and oligonucleotide primers; (d) covering the microchip produced in (c) with a substrate comprising a hydrophobic surface, under conditions under which the hydrophobic surface contacts the microwells of (c); (e) maintaining the microwells that contain a single cell and PCR enzymes and PCR oligonucleotides under conditions under which the cleavable linkers of the surface target-bound RPCs in the microwells are cleaved and the reporter molecules are released from the cells to which RPCs are bound to a target on their surface; (f) amplifying the cleaved nucleic acid reporter molecules of (e) by PCR, thereby producing a plurality of amplification products in each microwell; (f) amplifying the cleaved nucleic acid reporter molecules of (e) by PCR, thereby producing a plurality of amplification products in each microwell; (g) lowering the temperature inside the microwells of (f) and providing conditions under which the amplification products of (f) do not interact with the substrate of (d); (h) maintaining the conditions of (g) and removing the substrate of (d) from the microchip; (i) covering the microchip produced in (h) with a substrate bearing a microarray comprising nucleic acid probes complementary to the amplification products of (f) and arrayed in a known spatial arrangement; (j) combining the amplification products of (f) with the nucleic acid probes complementary to the amplification products under conditions under which the amplification products and the nucleic acid probes hybridize on the microarray of the substrate and produce amplification product-nucleic acid probe complexes bound to the substrate; (k) identifying microwells of (f) that each contain a pool of individual cells; (l) removing the substrate bearing the complexes produced in (j) from the microchip; and (m) detecting whether nucleic acid-nucleic acid probe complexes are bound to the substrate, and if complexes are bound determining that cell surface targets are present on members of the pool of individual cells. In some embodiments, the identity of the intracellular target is determined with reference to the position of the complementary nucleic acid on the microarray, which specifies the target identity.

In some embodiments the method of multiplexed detecting of more than one low abundance intracellular target from an individual cell comprises (a) producing a suspension of fixed, permeabilized cells; (b) incubating cells with at least two reporter-probe conjugates (RPC) each of which comprises, in the following order: (1) a nucleic acid bait that hybridizes to a low abundance intracellular target; (2) a cleavable linker; and (3) a nucleic acid reporter molecule of known sequence, under conditions under which nucleic acid bait components of the RPCs bind to their intracellular targets, thereby producing cells comprising intracellular target-bound RPCs; (c) washing the product of (b) to remove unbound RPCs and produce a suspension of cells that bear (have bound to intracellular targets) a RPC; (d) loading (1) the suspension produced in (c); and (2) PCR enzymes and PCR oligonucleotide primers complementary to the nucleic acid reporter molecule of (b)(3) onto a microchip comprising nanoliter microwells, thereby producing a microchip comprising nanoliter microwells that contain a single cell and PCR enzymes and oligonucleotide primers; (e) covering the microchip produced in (d) with a substrate comprising a hydrophobic surface under conditions under which the hydrophobic surface contacts the microwells of (d); (f) maintaining the microwells that contain a single cell and PCR enzymes and PCR oligonucleotides under conditions under which the cleavable linkers of the surface target-bound RPCs in the microwells are cleaved and the reporter molecules are released from the cells to which RPCs are bound to an intracellular target; (g) amplifying the released nucleic acid reporter molecules of (f) by PCR, thereby producing a plurality of amplification products in each microwell; (h) lowering the temperature inside the microwells of (g) and providing conditions under which the amplification products of (g) do not interact with the substrate of (e); (i) maintaining the conditions of (h) and removing the substrate of (d) from the microchip; (j) covering the microchip produced in (h) with a substrate bearing a microarray comprising nucleic acid probes complementary to the amplification products of (g) and arrayed in a known spatial arrangement; (k) providing conditions under which the amplification products of (g) hybridize to the nucleic acid probes of (j) and produce amplification product-nucleic acid probe complexes bound to the substrate; (l) identifying microwells of (f) containing a single cell; (m) removing the substrate bearing the complexes produced in (k) from the microchip; and, (n) detecting whether nucleic acid-nucleic acid probe complexes are bound to the substrate, and if complexes are bound determining that intracellular targets are present. After hybridization of the reporter molecule nucleic acid to the complementary nucleic acid on the microarray occurs, the identity of the intracellular target is determined with reference to the position of the complementary nucleic acid on the microarray, which specifies the target identity. For example, intracellular phosphoproteins such as p-mTOR are important signal transduction proteins and are present at low abundance as compared to total mTOR. Detecting these phosphoproteins rather than total proteins directly correlate to the activation of corresponding signaling cascades.

In some embodiments, the method of multiplexed detecting of more than one low abundance intracellular target from each member of a pool of cells comprises: (a) producing a suspension of fixed, permeabilized cells; (b) incubating cells with at least two reporter-probe conjugates (RPC) each of which comprises, in the following order: (1) a nucleic acid bait that hybridizes to a low abundance intracellular target; (2) a cleavable linker; and (3) a nucleic acid reporter molecule of known sequence, under conditions under which nucleic acid bait components of the RPCs bind to their intracellular targets, thereby producing cells comprising intracellular target-bound RPCs; (c) washing the product of (b) to remove unbound RPCs and produce a suspension of cells that bear (have bound to intracellular targets) a RPC; (d) loading (1) the suspension produced in (c); and (2) PCR enzymes and PCR oligonucleotide primers complementary to the nucleic acid reporter molecule of (b)(3) onto a microchip comprising nanoliter microwells, thereby producing a microchip comprising nanoliter microwells that each contain a pool of individual cells and PCR enzymes and oligonucleotide primers; (e) covering the microchip produced in (d) with a substrate comprising a hydrophobic surface under conditions under which the hydrophobic surface contacts the microwells of (d); (f) maintaining the microwells that contain a single cell and PCR enzymes and PCR oligonucleotides under conditions under which the cleavable linkers of the surface target-bound RPCs in the microwells are cleaved and the reporter molecules are released from the cells to which RPCs are bound to an intracellular target; (g) amplifying the released nucleic acid reporter molecules of (f) by PCR, thereby producing a plurality of amplification products in each microwell; (h) lowering the temperature inside the microwells of (g) and providing conditions under which the amplification products of (g) do not interact with the substrate of (e); (i) maintaining the conditions of (h) and removing the substrate of (d) from the microchip; (j) covering the microchip produced in (h) with a substrate bearing a microarray comprising nucleic acid probes complementary to the amplification products of (g) and arrayed in a known spatial arrangement; (k) providing conditions under which the amplification products of (g) hybridize to the nucleic acid probes of (j) and produce amplification product-nucleic acid probe complexes bound to the substrate; (l) identifying microwells of (f) each containing a pool of individual cells; (m) removing the substrate bearing the complexes produced in (k) from the microchip; and, (n) detecting whether nucleic acid-nucleic acid probe complexes are bound to the substrate, and if complexes are bound determining that intracellular targets are present on members of the pool of individual cells. After hybridization of the reporter molecule nucleic acid to the complementary nucleic acid on the microarray occurs, the identity of the intracellular target is determined with reference to the position of the complementary nucleic acid on the microarray, which specifies the target identity.

In some embodiments, the pool of cells comprises between about 2 and about 100 cells. In some embodiments, the pool of cells comprises 2, or 3, or 4, or 5, or 6, or 7, or 8, or 9, or 10 cells.

In some embodiments, the cells of (a) are incubated with 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, or 45 RPCs.

In some embodiments, the antibody of each RPC is a polyclonal antibody. In some embodiments, the antibody of each RPC is a monoclonal antibody. In some embodiments, the antibody of each RPC is a chimeric antibody. In some embodiments, the antibody of each RPC is a humanized antibody. In some embodiments, the antibody of each RPC is selected from the group consisting of CD3, CD4, CD8, CD11, CD24, EPCAM, and PSMA.

In some embodiments, the nucleic acid bait of each RPC is between about 10 and about 500 nucleotides in length. In some embodiments, the nucleic acid bait of each RPC is between about 10 and about 30 nucleotides in length. In some embodiments, the nucleotide bait of each RPC is 10, 11, 12, 13, 14, 15, 16, 17, 18, 19, 20, 21, 22, 23, 24, 25, 26, 27, 28, 29, or 30 nucleotides in length.

In some embodiments, the cleavable linker of each RPC is photocleavable. In some embodiments, the cleavable linker of each RPC is enzyme cleavable.

In some embodiments, the reporter molecule of each RPC is between about 10 and about 500 nucleotides in length. In some embodiments, the reporter molecule of each RPC is between about 10 and about 30 nucleotides in length. In some embodiments, the reporter molecule of each RPC is 10, 11, 12, 13, 14, 15, 16, 17, 18, 19, 20, 21, 22, 23, 24, 25, 26, 27, 28, 29, or 30 nucleotides in length.

In some embodiments, the microchip comprising nanoliter microwells is made of polydimethylsiloxane (PDMS). In some embodiments, the volume of the nanoliter wells of the microchip comprising nanoliter microwells is between about 1 nL and 999 nL. In some embodiments, the substrate used to cover the microchip is glass. In some embodiments, the substrate used to cover the microchip bears a microarray comprising nucleic acid probes complementary to the known nucleic acid sequences of the RPC reporter probes, and arrayed in a known spatial arrangement. In some embodiments, the substrate used to cover the microchip bears a microarray comprising nucleic acid probes complementary to PCR amplicons of the known nucleic acid sequences of the RPC reporter probes, and arrayed in a known spatial arrangement. In some embodiments, the substrate used to cover the microchip has a hydrophobic surface. In some embodiments, the hydrophobic surface of the substrate used to cover the microchip is Teflon®. In some embodiments, the hydrophobic surface of the substrate used to cover the microchip is alkane long chain functionalized silicon oxide surface or metal surfaces.

In some embodiments, the temperature of the microwells is lowered below 0° C. In some embodiments, the temperature of the microwells is lowered below −10° C. In some embodiments, the temperature of the microwells is lowered by between about 20° C. and 100° C. In some embodiments, the temperature of the microwells is lowered over a time span of 1 ms to 5 minutes. In some embodiments, the temperature of the microwells is lowered over a time span of 0.5 ms to 2 minutes. In some embodiments, the temperature of the microwells is lowered over a time span of is to 1 minute.

In some embodiments, the detecting of the reporter probe-nucleic acid probe complexes is performed by microarray scanning. In some embodiments, the detecting of the PCR amplicon-nucleic acid probe complexes is performed by microarray scanning.

The present disclosure, in some embodiments, is related to methods of multiplexed detection of cell surface and/or intracellular targets on or in a single cell or a pool of individual cells. The present method also relates to detecting more than one cell surface target and/or intracellular target, on or in a single cell or a pool of individual cells. In some embodiments, the method of multiplexed detecting of more than one cell surface target on an individual cell comprises: (a) incubating cells with at least two reporter-probe conjugates (RPC), each of which comprises, in the following order: (1) an antibody that binds a cell surface target; (2) a cleavable linker; and (3) a nucleic acid reporter molecule of known sequence, under conditions under which antibody components of the RPCs bind to their cell surface targets, thereby producing cells to which RPCs are bound to a target on their surface; (b) washing the product of (a) to remove unbound RPCs and produce a suspension of cells that bear (have bound to their surface) a RPC; (c) loading the suspension produced in (b) onto a microchip comprising nanoliter microwells and producing a microchip comprising nanoliter microwells that contain a single cell; (d) covering the microchip produced in (c) with a substrate bearing a microarray comprising nucleic acid probes complementary to the nucleic acid reporter molecules of (a)(3) and arrayed in a known spatial arrangement; (e) identifying microwells of (d) that contain a single cell; (f) maintaining the microwells that contain a single cell under conditions under which the cleavable linkers of the surface target-bound RPCs in the microwells are cleaved and the reporter molecules are released from the cells to which RPCs are bound to a target on their surface, and the released reporter molecules hybridize to complementary nucleic acid probes on the microarray and produce reporter molecule nucleic acid-nucleic acid probe complexes bound to the substrate; (g) removing the substrate bearing the complexes produced in (f) from the microchip; and (h) detecting whether nucleic acid-nucleic acid probe complexes are bound to the substrate, and if complexes are bound, determining that cell surface targets are present on the cell. In some embodiments, the identity of the intracellular target is determined with reference to the position of the complementary nucleic acid on the microarray, which specifies the target identity. For example, the combination of surface antigens CD3 and CD8 can define the cytotoxic T lymphocytes. Surface antigens such as CD3, CD4, CD8, CD11a, CD11b, CD12 and CD24 can be measured together to distinguish different immune cell phenotypes.

In some embodiments, the method of multiplexed detecting of more than one cell surface target on each member of a pool of individual cells comprises: (a) incubating the cells with at least two reporter-probe conjugates (RPC) each of which comprises, in the following order: (1) an antibody that binds a cell surface target; (2) a cleavable linker; and (3) a nucleic acid reporter molecule of known sequence, under conditions under which antibody components of the RPCs bind to their cell surface targets, thereby producing cells to which RPCs are bound to a target on their surface; (b) washing the product of (a) to remove unbound RPCs and produce a suspension of cells that bear (have bound to their surface) a RPC; (c) loading the suspension produced in (b) onto a microchip comprising nanoliter microwells and producing a microchip comprising nanoliter microwells that each contain a pool of individual cells; (d) covering the microchip produced in (c) with a substrate bearing a microarray comprising nucleic acid probes complementary to the nucleic acid reporter molecules of (a)(3) and arrayed in a known spatial arrangement; (e) identifying microwells of (d) that contain a pool of individual cells; (f) maintaining the microwells that each contain a pool of individual cells under conditions under which the cleavable linkers of the surface target-bound RPCs in the microwells are cleaved and the reporter molecules are released from each member of the pool of individual cells to which RPCs are bound to a target on their surface, and the released reporter molecules hybridize to complementary nucleic acid probes on the microarray and produce reporter molecule nucleic acid-nucleic acid probe complexes bound to the substrate; (g) removing the substrate bearing the complexes produced in (f) from the microchip; and (h) detecting whether nucleic acid-nucleic acid probe complexes are bound to the substrate, and if complexes are bound, determining that cell surface targets are present on members of the pool of individual cells. In some embodiments, the identity of the intracellular target is determined with reference to the position of the complementary nucleic acid on the microarray, which specifies the target identity. In some embodiments, the pool of cells comprises a single cell type. In some embodiments, the pool of cells comprises multiple cell types.

In some embodiments, the method of multiplexed detecting of more than one intracellular target in an individual cell comprises: (a) producing a suspension of fixed, permeabilized cells; (b) incubating cells of (a) with at least two reporter-probe conjugates (RPC) each of which comprises, in the following order: (1) a nucleic acid bait that hybridizes to an intracellular target; (2) a cleavable linker; and (3) a nucleic acid reporter molecule of known sequence, under conditions under which nucleic acid bait components of the RPCs bind to their intracellular targets, thereby producing cells comprising intracellular target-bound RPCs; (c) washing the product of (b) to remove unbound RPCs and produce a suspension of cells that bear (have bound to intracellular targets) a RPC; (d) loading the suspension produced in (c) onto a microchip comprising nanoliter microwells and producing a microchip comprising nanoliter microwells that contain a single cell; (e) covering the microchip produced in (d) with a substrate bearing a microarray comprising nucleic acid probes complementary to the nucleic acid reporter molecules of (b)(3) and arrayed in a known spatial arrangement; (f) identifying microwells of (e) containing a single cell; (g) maintaining the microwells that contain a single cell under conditions under which the cleavable linkers of the intracellular target-bound RPCs in the microwells are cleaved and the reporter molecules are released from the cells to which RPCs are bound to an intracellular target, and the released reporter molecules hybridize to complementary nucleic acid probes on the microarray and produce reporter molecule nucleic acid-nucleic acid probe complexes bound to the substrate; (h) removing the substrate bearing the complexes produced in (g) from the microchip; and (i) determining whether nucleic acid-nucleic acid probe complexes are bound to the substrate, and if complexes are bound, determining that cell surface targets are present on the cell. In some embodiments, the identity of the intracellular target is determined with reference to the position of the complementary nucleic acid on the microarray, which specifies the target identity. For example, the detection of intracellular proteins such as p-Akt can determine the proliferation potential of a give type of cancer cells. Detecting a panel of intracellular proteins such as pEGFR, pERK and pS6 can distinguish the differential roles of Ras and Pi3K-Akt pathways in determining the fate of individual cells including a heterogeneous population of cancer cells.

In some embodiments, the method of multiplexed detecting of more than one intracellular target on each member of a pool of individual cells comprises: (a) producing a suspension of fixed, permeabilized cells; (b) incubating cells of (a) with at least two reporter-probe conjugates (RPC) each of which comprises, in the following order: (1) a nucleic acid bait that hybridizes to an intracellular target; (2) a cleavable linker; and (3) a nucleic acid reporter molecule of known sequence, under conditions under which nucleic acid bait components of the RPCs bind to their intracellular targets, thereby producing cells comprising intracellular target-bound RPCs; (c) washing the product of (b) to remove unbound RPCs and produce a suspension of cells that bear (have bound to intracellular targets) a RPC; (d) loading the suspension produced in (c) onto a microchip comprising nanoliter microwells and producing a microchip comprising nanoliter microwells that each contain a pool of individual cells; (e) covering the microchip produced in (d) with a substrate bearing a microarray comprising nucleic acid probes complementary to the nucleic acid reporter molecules of (b)(3) and arrayed in a known spatial arrangement; (f) identifying microwells of (e) that each contain a pool of individual cells; (g) maintaining the microwells that contain a single cell under conditions under which the cleavable linkers of the intracellular target-bound RPCs in the microwells are cleaved and the reporter molecules are released from each member of the pool of individual cells to which RPCs are bound to an intracellular target, and the released reporter molecules hybridize to complementary nucleic acid probes on the microarray and produce reporter molecule nucleic acid-nucleic acid probe complexes bound to the substrate; (h) removing the substrate bearing the complexes produced in (g) from the microchip; and (i) detecting whether nucleic acid-nucleic acid probe complexes are bound to the substrate, and if complexes are bound, determining that intracellular targets are present inside members of the pool of individual cells. In some embodiments, the identity of the intracellular target is determined with reference to the position of the complementary nucleic acid on the microarray, which specifies the target identity. In some embodiments, the pool of cells comprises a single cell type. In some embodiments, the pool of cells comprises multiple cell types. For example, the detection of intracellular proteins such as p-Akt can determine the proliferation potential of a give type of cancer cells. Detecting a panel of intracellular proteins such as pEGFR, pERK and pS6 can distinguish the differential roles of Ras and Pi3K-Akt pathways in determining the fate of individual cells including a heterogeneous population of cancer cells.

In some embodiments, the method of multiplexed detecting more than one of low abundance cell surface targets of an individual cell comprises: (a) incubating cells with at least two reporter-probe conjugates (RPC) each of which comprises, in the following order: (1) an antibody that binds to a low abundance cell surface target; (2) a cleavable linker; and (3) a nucleic acid reporter molecule of known sequence, under conditions under which antibody components of the RPCs bind to their cell surface targets, thereby producing cells to which RPCs are bound to a target on their surface; (b) washing the product of (a) to remove unbound RPCs and produce a suspension of cells that bear (have bound to their surface) a RPC; (c) loading (1) the suspension produced in (b); and (2) PCR enzymes and PCR oligonucleotide primers complementary to the nucleic acid reporter molecule of (b)(3) onto a microchip comprising nanoliter microwells, thereby producing a microchip comprising nanoliter microwells that contain a single cell and PCR enzymes and oligonucleotide primers; (d) covering the microchip produced in (c) with a substrate comprising a hydrophobic surface, under conditions under which the hydrophobic surface contacts the microwells of (c); (e) maintaining the microwells that contain a single cell and PCR enzymes and PCR oligonucleotides under conditions under which the cleavable linkers of the surface target-bound RPCs in the microwells are cleaved and the reporter molecules are released from the cells to which RPCs are bound to a target on their surface; (f) amplifying the cleaved nucleic acid reporter molecules of (e) by PCR, thereby producing a plurality of amplification products in each microwell; (g) lowering the temperature inside the microwells of (f) and providing conditions under which the amplification products of (f) do not interact with the substrate of (d); (h) maintaining the conditions of (g) and removing the substrate of (d) from the microchip; (i) covering the microchip produced in (h) with a substrate bearing a microarray comprising nucleic acid probes complementary to the amplification products of (f) and arrayed in a known spatial arrangement; (j) combining the amplification products of (f) with the nucleic acid probes complementary to the amplification products under conditions under which the amplification products and the nucleic acid probes hybridize on the microarray of the substrate and produce amplification product-nucleic acid probe complexes bound to the substrate; (k) identifying microwells of (f) containing a single cell; (l) removing the substrate bearing the complexes produced in (j) from the microchip; and (m) detecting whether nucleic acid-nucleic acid probe complexes are bound to the substrate, and if complexes are bound determining that cell surface targets are present on the cell. In some embodiments, the identity of the intracellular target is determined with reference to the position of the complementary nucleic acid on the microarray, which specifies the target identity. For example, surface antigen PD-1, which is immune check point protein, has a very wide range of expression levels. The ability to detect low abundance expression of PD-1 is of significance in determining the activation state of individual immune cells.

In some embodiments, the method of multiplexed detecting of more than one low abundance cell surface target on each member of a pool of cells comprises: (a) incubating cells with at least two reporter-probe conjugates (RPC) each of which comprises, in the following order: (1) an antibody that binds to a low abundance cell surface target; (2) a cleavable linker; and (3) a nucleic acid reporter molecule of known sequence, under conditions under which antibody components of the RPCs bind to their cell surface targets, thereby producing cells to which RPCs are bound to a target on their surface; (b) washing the product of (a) to remove unbound RPCs and produce a suspension of cells that bear (have bound to their surface) a RPC; (c) loading (1) the suspension produced in (b); and (2) PCR enzymes and PCR oligonucleotide primers complementary to the nucleic acid reporter molecule of (b)(3) onto a microchip comprising nanoliter microwells, thereby producing a microchip comprising nanoliter microwells that each contain a pool of individual cells and PCR enzymes and oligonucleotide primers; (d) covering the microchip produced in (c) with a substrate comprising a hydrophobic surface, under conditions under which the hydrophobic surface contacts the microwells of (c); (e) maintaining the microwells that contain a single cell and PCR enzymes and PCR oligonucleotides under conditions under which the cleavable linkers of the surface target-bound RPCs in the microwells are cleaved and the reporter molecules are released from the cells to which RPCs are bound to a target on their surface; (f) amplifying the cleaved nucleic acid reporter molecules of (e) by PCR, thereby producing a plurality of amplification products in each microwell; (f) amplifying the cleaved nucleic acid reporter molecules of (e) by PCR, thereby producing a plurality of amplification products in each microwell; (g) lowering the temperature inside the microwells of (f) and providing conditions under which the amplification products of (f) do not interact with the substrate of (d); (h) maintaining the conditions of (g) and removing the substrate of (d) from the microchip; (i) covering the microchip produced in (h) with a substrate bearing a microarray comprising nucleic acid probes complementary to the amplification products of (f) and arrayed in a known spatial arrangement; (j) combining the amplification products of (f) with the nucleic acid probes complementary to the amplification products under conditions under which the amplification products and the nucleic acid probes hybridize on the microarray of the substrate and produce amplification product-nucleic acid probe complexes bound to the substrate; (k) identifying microwells of (f) that each contain a pool of individual cells; (l) removing the substrate bearing the complexes produced in (j) from the microchip; and (m) detecting whether nucleic acid-nucleic acid probe complexes are bound to the substrate, and if complexes are bound determining that cell surface targets are present on members of the pool of individual cells. In some embodiments, the identity of the intracellular target is determined with reference to the position of the complementary nucleic acid on the microarray, which specifies the target identity.

In some embodiments the method of multiplexed detecting of more than one low abundance intracellular target from an individual cell comprises (a) producing a suspension of fixed, permeabilized cells; (b) incubating cells with at least two reporter-probe conjugates (RPC) each of which comprises, in the following order: (1) a nucleic acid bait that hybridizes to a low abundance intracellular target; (2) a cleavable linker; and (3) a nucleic acid reporter molecule of known sequence, under conditions under which nucleic acid bait components of the RPCs bind to their intracellular targets, thereby producing cells comprising intracellular target-bound RPCs; (c) washing the product of (b) to remove unbound RPCs and produce a suspension of cells that bear (have bound to intracellular targets) a RPC; (d) loading (1) the suspension produced in (c); and (2) PCR enzymes and PCR oligonucleotide primers complementary to the nucleic acid reporter molecule of (b)(3) onto a microchip comprising nanoliter microwells, thereby producing a microchip comprising nanoliter microwells that contain a single cell and PCR enzymes and oligonucleotide primers; (e) covering the microchip produced in (d) with a substrate comprising a hydrophobic surface under conditions under which the hydrophobic surface contacts the microwells of (d); (f) maintaining the microwells that contain a single cell and PCR enzymes and PCR oligonucleotides under conditions under which the cleavable linkers of the surface target-bound RPCs in the microwells are cleaved and the reporter molecules are released from the cells to which RPCs are bound to an intracellular target; (g) amplifying the released nucleic acid reporter molecules of (f) by PCR, thereby producing a plurality of amplification products in each microwell; (h) lowering the temperature inside the microwells of (g) and providing conditions under which the amplification products of (g) do not interact with the substrate of (e); (i) maintaining the conditions of (h) and removing the substrate of (d) from the microchip; (j) covering the microchip produced in (h) with a substrate bearing a microarray comprising nucleic acid probes complementary to the amplification products of (g) and arrayed in a known spatial arrangement; (k) providing conditions under which the amplification products of (g) hybridize to the nucleic acid probes of (j) and produce amplification product-nucleic acid probe complexes bound to the substrate; (l) identifying microwells of (f) containing a single cell; (m) removing the substrate bearing the complexes produced in (k) from the microchip; and, (n) detecting whether nucleic acid-nucleic acid probe complexes are bound to the substrate, and if complexes are bound determining that intracellular targets are present. After hybridization of the reporter molecule nucleic acid to the complementary nucleic acid on the microarray occurs, the identity of the intracellular target is determined with reference to the position of the complementary nucleic acid on the microarray, which specifies the target identity. For example, intracellular phosphoproteins such as p-mTOR are important signal transduction proteins and are present at low abundance as compared to total mTOR. Detecting these phosphoproteins rather than total proteins directly correlate to the activation of corresponding signaling cascades.

In some embodiments, the method of multiplexed detecting of more than one low abundance intracellular target from each member of a pool of cells comprises: (a) producing a suspension of fixed, permeabilized cells; (b) incubating cells with at least two reporter-probe conjugates (RPC) each of which comprises, in the following order: (1) a nucleic acid bait that hybridizes to a low abundance intracellular target; (2) a cleavable linker; and (3) a nucleic acid reporter molecule of known sequence, under conditions under which nucleic acid bait components of the RPCs bind to their intracellular targets, thereby producing cells comprising intracellular target-bound RPCs; (c) washing the product of (b) to remove unbound RPCs and produce a suspension of cells that bear (have bound to intracellular targets) a RPC; (d) loading (1) the suspension produced in (c); and (2) PCR enzymes and PCR oligonucleotide primers complementary to the nucleic acid reporter molecule of (b)(3) onto a microchip comprising nanoliter microwells, thereby producing a microchip comprising nanoliter microwells that each contain a pool of individual cells and PCR enzymes and oligonucleotide primers; (e) covering the microchip produced in (d) with a substrate comprising a hydrophobic surface under conditions under which the hydrophobic surface contacts the microwells of (d); (f) maintaining the microwells that contain a single cell and PCR enzymes and PCR oligonucleotides under conditions under which the cleavable linkers of the surface target-bound RPCs in the microwells are cleaved and the reporter molecules are released from the cells to which RPCs are bound to an intracellular target; (g) amplifying the released nucleic acid reporter molecules of (f) by PCR, thereby producing a plurality of amplification products in each microwell; (h) lowering the temperature inside the microwells of (g) and providing conditions under which the amplification products of (g) do not interact with the substrate of (e); (i) maintaining the conditions of (h) and removing the substrate of (d) from the microchip; (j) covering the microchip produced in (h) with a substrate bearing a microarray comprising nucleic acid probes complementary to the amplification products of (g) and arrayed in a known spatial arrangement; (k) providing conditions under which the amplification products of (g) hybridize to the nucleic acid probes of (j) and produce amplification product-nucleic acid probe complexes bound to the substrate; (l) identifying microwells of (f) each containing a pool of individual cells; (m) removing the substrate bearing the complexes produced in (k) from the microchip; and, (n) detecting whether nucleic acid-nucleic acid probe complexes are bound to the substrate, and if complexes are bound determining that intracellular targets are present on members of the pool of individual cells. After hybridization of the reporter molecule nucleic acid to the complementary nucleic acid on the microarray occurs, the identity of the intracellular target is determined with reference to the position of the complementary nucleic acid on the microarray, which specifies the target identity.

In some embodiments, the pool of cells comprises between about 2 and about 100 cells. In some embodiments, the pool of cells comprises 2, or 3, or 4, or 5, or 6, or 7, or 8, or 9, or 10 cells.

In some embodiments, the cells of (a) are incubated with 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, or 45 RPCs.

In some embodiments, the antibody of each RPC is a polyclonal antibody. In some embodiments, the antibody of each RPC is a monoclonal antibody. In some embodiments, the antibody of each RPC is a chimeric antibody. In some embodiments, the antibody of each RPC is a humanized antibody. In some embodiments, the antibody of each RPC is selected from the group consisting of CD3, CD4, CD8, CD11, CD24, EPCAM, and PSMA.

In some embodiments, the nucleic acid bait of each RPC is between about 10 and about 500 nucleotides in length. In some embodiments, the nucleic acid bait of each RPC is between about 10 and about 30 nucleotides in length. In some embodiments, the nucleotide bait of each RPC is 10, 11, 12, 13, 14, 15, 16, 17, 18, 19, 20, 21, 22, 23, 24, 25, 26, 27, 28, 29, or 30 nucleotides in length.

In some embodiments, the cleavable linker of each RPC is photocleavable. In some embodiments, the cleavable linker of each RPC is enzyme cleavable.

In some embodiments, the reporter molecule of each RPC is between about 10 and about 500 nucleotides in length. In some embodiments, the reporter molecule of each RPC is between about 10 and about 30 nucleotides in length. In some embodiments, the reporter molecule of each RPC is 10, 11, 12, 13, 14, 15, 16, 17, 18, 19, 20, 21, 22, 23, 24, 25, 26, 27, 28, 29, or 30 nucleotides in length.

In some embodiments, the microchip comprising nanoliter microwells is made of polydimethylsiloxane (PDMS). In some embodiments, the volume of the nanoliter wells of the microchip comprising nanoliter microwells is between about 1 nL and 999 nL. In some embodiments, the substrate used to cover the microchip is glass. In some embodiments, the substrate used to cover the microchip bears a microarray comprising nucleic acid probes complementary to the known nucleic acid sequences of the RPC reporter probes, and arrayed in a known spatial arrangement. In some embodiments, the substrate used to cover the microchip bears a microarray comprising nucleic acid probes complementary to PCR amplicons of the known nucleic acid sequences of the RPC reporter probes, and arrayed in a known spatial arrangement. In some embodiments, the substrate used to cover the microchip has a hydrophobic surface. In some embodiments, the hydrophobic surface of the substrate used to cover the microchip is Teflon®. In some embodiments, the hydrophobic surface of the substrate used to cover the microchip is alkane long chain functionalized silicon oxide surface or metal surfaces.

In some embodiments, the temperature of the microwells is lowered below 0° C. In some embodiments, the temperature of the microwells is lowered below −10° C. In some embodiments, the temperature of the microwells is lowered by between about 20° C. and 100° C. In some embodiments, the temperature of the microwells is lowered over a time span of 1 ms to 5 minutes. In some embodiments, the temperature of the microwells is lowered over a time span of 0.5 ms to 2 minutes. In some embodiments, the temperature of the microwells is lowered over a time span of is to 1 minute.

In some embodiments, the detecting of the reporter probe-nucleic acid probe complexes is performed by microarray scanning. In some embodiments, the detecting of the PCR amplicon-nucleic acid probe complexes is performed by microarray scanning.

Additional Embodiments

1. A method of multiplexed detecting of more than one cell surface target of an individual cell comprising:
   (a) incubating cells with at least two reporter-probe conjugates (RPC) each of which comprises, in the following order: (1) an antibody that binds a cell surface target; (2) a cleavable linker; and (3) a nucleic acid reporter molecule of known sequence, under conditions under which antibody components of the RPCs bind to their cell surface targets, thereby producing cells to which RPCs are bound to their surface;
   (b) washing the product of (a) to remove unbound RPCs and produce a suspension of cells that bear (have bound to their surface) a RPC;
   (c) loading the suspension produced in (b) onto a microchip comprising nanoliter microwells and producing a microchip comprising nanoliter microwells that contain a single cell;
   (d) covering the microchip produced in (c) with a substrate bearing a microarray comprising nucleic acid probes complementary to the nucleic acid reporter molecules of (a)(3) and arrayed in a known spatial arrangement;
   (e) identifying microwells of (d) containing a single cell;
   (f) maintaining the conditions under which the cleavable linkers of the surface target-bound RPCs in the microwells of (e) are cleaved, releasing the reporter molecule from the target-bound antibody, under conditions under which nucleic acid reporter molecules of the RPCs hybridize to complementary nucleic acid probes on the microarray and produce reporter molecule nucleic acid-nucleic acid probe complexes bound to the substrate;
   (g) removing the substrate bearing the complexes produced in (f) from the microchip; and
   (h) detecting the location of nucleic acid-nucleic acid probe complexes bound to the substrate and determining if cell surface targets are present.

2. A method of multiplexed detection of cell surface targets of a pool of cells comprising:
   (a) incubating the cells with at least two reporter-probe conjugates (RPC) each of which comprises, in the following order: (1) an antibody that binds a cell surface target; (2) a cleavable linker; and (3) a nucleic acid reporter molecule of known sequence, under conditions under which antibody components of the RPCs bind to their cell surface targets, thereby producing cells to which RPCs are bound to a target on their surface;
   (b) washing the product of (a) to remove unbound RPCs and produce a suspension of cells that bear (have bound to their surface) a RPC;
   (c) loading the suspension produced in (b) onto a microchip comprising nanoliter microwells and producing a microchip comprising nanoliter microwells that each contain a pool of individual cells;
   (d) covering the microchip produced in (c) with a substrate bearing a microarray comprising nucleic acid probes complementary to the nucleic acid reporter molecules of (a)(3) and arrayed in a known spatial arrangement;

(e) identifying microwells of (d) that contain a pool of individual cells;

(f) maintaining the microwells that each contain a pool of individual cells under conditions under which the cleavable linkers of the surface target-bound RPCs in the microwells are cleaved and the reporter molecules are released from each member of the pool of individual cells to which RPCs are bound to a target on their surface, and the released reporter molecules hybridize to complementary nucleic acid probes on the microarray and produce reporter molecule nucleic acid-nucleic acid probe complexes bound to the substrate;

(g) removing the substrate bearing the complexes produced in (f) from the microchip; and (h) detecting whether nucleic acid-nucleic acid probe complexes are bound to the substrate, and if complexes are bound, determining that cell surface targets are present on members of the pool of individual cells.

3. The method of embodiment 2, wherein the pool of cells comprises between about 2 and about 100 cells.

4. The method of embodiment 3, wherein the pool of cells comprises 2, or 3, or 4, or 5, or 6, or 7, or 8, or 9, or 10 cells.

5. The method of any one of embodiments 1 to 4, wherein the cells of (a) are incubated with 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, or 45 RPCs.

6. The method of any one of embodiments 1 to 5, wherein the antibody of (a)(1) is a polyclonal antibody.

7. The method of any one of embodiments 1 to 5, wherein the antibody of (a)(1) is a monoclonal antibody.

8. The method of any one of embodiments 1 to 7, wherein the antibody of (a)(1) is a chimeric antibody.

9. The method of embodiment 8, wherein the antibody of (a)(1) is a humanized antibody. 10. The method of any one of embodiments 1 to 9, wherein the antibody of (a)(1) is selected from the group consisting of antibodies against CD3, CD4, CD8, CD11, CD24, EPCAM, and PSMA.

11. The method of any one of embodiments 1 to 10, wherein the cleavable linker of (a)(2) is photocleavable.

12. The method of any one of embodiments 1 to 10, wherein the cleavable linker of (a)(2) is enzyme cleavable.

13. The method of any one of embodiments 1 to 13, wherein the reporter molecule of (a)(3) is between about 10 and about 500 nucleotides in length.

14. The method of any one of embodiments 1 to 13, wherein the reporter molecule of (a)(3) is between about 10 and about 30 nucleotides in length.

15. The method of any one of embodiments 1 to 14, wherein the reporter molecule of (a)(3) is 10, 11, 12, 13, 14, 15, 16, 17, 18, 19, 20, 21, 22, 23, 24, 25, 26, 27, 28, 29, or 30 nucleotides in length.

16. The method of any one of embodiments 1 to 15, wherein the microchip of (c) is made of polydimethylsiloxane (PDMS).

17. The method of any one of embodiments 1 to 16, wherein the volume of the nanoliter wells of the microchip of (c) is between about 1 nL and 999 nL.

18. The method of any one of embodiments 1 to 17, wherein the detecting of (h) is performed by microarray scanning.

19. A method of multiplexed detection of low abundance cell surface targets of an individual cell comprising:

(a) incubating cells with at least two reporter-probe conjugates (RPC) each of which comprises, in the following order: (1) an antibody that binds to a low abundance cell surface target; (2) a cleavable linker; and (3) a nucleic acid reporter molecule of known sequence, under conditions under which antibody components of the RPCs bind to their cell surface targets, thereby producing cells to which RPCs are bound to a target on their surface;

(b) washing the product of (a) to remove unbound RPCs and produce a suspension of cells that bear (have bound to their surface) a RPC;

(c) loading (1) the suspension produced in (b); and (2) PCR enzymes and PCR oligonucleotide primers complementary to the nucleic acid reporter molecule of (b)(3) onto a microchip comprising nanoliter microwells, thereby producing a microchip comprising nanoliter microwells that contain a single cell and PCR enzymes and oligonucleotide primers;

(d) covering the microchip produced in (c) with a substrate comprising a hydrophobic surface, under conditions under which the hydrophobic surface contacts the microwells of (c);

(e) maintaining the microwells that contain a single cell and PCR enzymes and PCR oligonucleotides under conditions under which the cleavable linkers of the surface target-bound RPCs in the microwells are cleaved and the reporter molecules are released from the cells to which RPCs are bound to a target on their surface;

(f) amplifying the cleaved nucleic acid reporter molecules of (e) by PCR, thereby producing a plurality of amplification products in each microwell;

(g) lowering the temperature inside the microwells of (f) and providing conditions under which the amplification products of (f) do not interact with the substrate of (d);

(h) maintaining the conditions of (g) and removing the substrate of (d) from the microchip;

(i) covering the microchip produced in (h) with a substrate bearing a microarray comprising nucleic acid probes complementary to the amplification products of (f) and arrayed in a known spatial arrangement;

(j) combining the amplification products of (f) with the nucleic acid probes complementary to the amplification products under conditions under which the amplification products and the nucleic acid probes hybridize on the microarray of the substrate and produce amplification product-nucleic acid probe complexes bound to the substrate;

(k) identifying microwells of (f) containing a single cell;

(l) removing the substrate bearing the complexes produced in (j) from the microchip; and (m) detecting whether nucleic acid-nucleic acid probe complexes are bound to the substrate, and if complexes are bound determining that cell surface targets are present on the cell.

20. A method of multiplexed detection of low abundance cell surface targets of a pool of cells comprising:

(a) incubating cells with at least two reporter-probe conjugates (RPC) each of which comprises, in the following order: (1) an antibody that binds to a low abundance cell surface target; (2) a cleavable linker; and (3) a nucleic acid reporter molecule of known sequence, under conditions under which antibody components of the RPCs bind to their cell surface targets, thereby producing cells to which RPCs are bound to a target on their surface;

(b) washing the product of (a) to remove unbound RPCs and produce a suspension of cells that bear (have bound to their surface) a RPC;

(c) loading (1) the suspension produced in (b); and (2) PCR enzymes and PCR oligonucleotide primers complementary to the nucleic acid reporter molecule of (b)(3) onto a microchip comprising nanoliter microwells, thereby producing a microchip comprising nanoliter microwells that each contain a pool of individual cells and PCR enzymes and oligonucleotide primers;

(d) covering the microchip produced in (c) with a substrate comprising a hydrophobic surface, under conditions under which the hydrophobic surface contacts the microwells of (c);

(e) maintaining the microwells that contain a single cell and PCR enzymes and PCR oligonucleotides under conditions under which the cleavable linkers of the surface target-bound RPCs in the microwells are cleaved and the reporter molecules are released from the cells to which RPCs are bound to a target on their surface;

(f) amplifying the cleaved nucleic acid reporter molecules of (e) by PCR, thereby producing a plurality of amplification products in each microwell; (f) amplifying the cleaved nucleic acid reporter molecules of (e) by PCR, thereby producing a plurality of amplification products in each microwell;

(g) lowering the temperature inside the microwells of (f) and providing conditions under which the amplification products of (f) do not interact with the substrate of (d);

(h) maintaining the conditions of (g) and removing the substrate of (d) from the microchip;

(i) covering the microchip produced in (h) with a substrate bearing a microarray comprising nucleic acid probes complementary to the amplification products of (f) and arrayed in a known spatial arrangement;

(j) combining the amplification products of (f) with the nucleic acid probes complementary to the amplification products under conditions under which the amplification products and the nucleic acid probes hybridize on the microarray of the substrate and produce amplification product-nucleic acid probe complexes bound to the substrate;

(k) identifying microwells of (f) that each contain a pool of individual cells;

(l) removing the substrate bearing the complexes produced in (j) from the microchip; and (m) detecting whether nucleic acid-nucleic acid probe complexes are bound to the substrate, and if complexes are bound determining that cell surface targets are present on members of the pool of individual cells.

21. The method of embodiment 20, wherein the pool of cells comprises between about 2 and about 100 cells.

22. The method of embodiment 21, wherein the pool of cells comprises 2, or 3, or 4, or 5, or 6, or 7, or 8, or 9, or 10 cells.

23. The method of any one of embodiments 19 to 22, wherein the cells of (a) are incubated with 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, or 45 RPCs.

24. The method of any one of embodiments 19 to 23, wherein the antibody of (a)(1) is a polyclonal antibody.

25. The method of any one of embodiments 19 to 23, wherein the antibody of (a)(1) is a monoclonal antibody.

26. The method of any one of embodiments 19 to 25, wherein the antibody of (a)(1) is a chimeric antibody.

27 The method of embodiment 26, wherein the antibody of (a)(1) is a humanized antibody.

28. The method of any one of embodiments 19 to 27, wherein the antibody of (a)(1) is selected from the group consisting of antibodies against CD3, CD4, CD8, CD11, CD24, EPCAM, and PSMA.

29. The method of any one of embodiments 19 to 28, wherein the cleavable linker of (a)(2) is photocleavable.

30. The method of any one of embodiments 19 to 28, wherein the cleavable linker of (a)(2) is enzyme cleavable.

31. The method of any one of embodiments 19 to 30, wherein the reporter molecule of (a)(3) is between about 10 and about 500 nucleotides in length.

32. The method of any one of embodiments 19 to 30, wherein the reporter molecule of (a)(3) is between about 10 and about 30 nucleotides in length.

33. The method of any one of embodiments 19 to 32, wherein the reporter molecule of (a)(3) is 10, 11, 12, 13, 14, 15, 16, 17, 18, 19, 20, 21, 22, 23, 24, 25, 26, 27, 28, 29, or 30 nucleotides in length.

34. The method of any one of embodiments 19 to 33, wherein the microchip of (c) is made of polydimethylsiloxane (PDMS).

35. The method of any one of embodiments 19 to 34, wherein the volume of the nanoliter wells of the microchip of (c) is between about 1 nL and 999 nL.

36. The method of any one of embodiments 19 to 35, wherein the detecting of (l) is performed by microarray scanning.

37. The method of any one of embodiments 19 to 36, wherein the substrate of (d) is glass.

38. The method of any one of embodiments 19 to 37, wherein the hydrophobic surface of the substrate of (d) is Teflon®.

39. The method of any one of embodiments 19 to 37, wherein the hydrophobic surface of the substrate of (d) is alkane chain functionalized silicone oxide surface and metal surface.

40. The method of any one of embodiments 19 to 39, wherein the temperature is lowered below 0° C.

41. The method of embodiment 40, wherein the temperature is lowered below −10° C. 42. The method of any one of embodiments 19 to 41, wherein the temperature is lowered by between about 20° C. and 100° C.

43. The method of any one of embodiments 19 to 42, wherein the temperature is lowered over a time span of 1 ms to 5 minutes.

44. The method of embodiment 43, wherein the temperature is lowered over a time span of 0.5 ms to 2 minutes.

45. The method of embodiment 44, wherein the temperature is lowered over a time span of 1 s to 1 minute.

46. A method of multiplexed detection of intracellular targets in an individual cell comprising:

(a) producing a suspension of fixed, permeabilized cells;

(b) incubating cells of (a) with at least two reporter-probe conjugates (RPC) each of which comprises, in the following order: (1) a nucleic acid bait that hybridizes to an intracellular target; (2) a cleavable linker; and (3) a nucleic acid reporter molecule of known sequence, under conditions under which nucleic acid bait components of the RPCs bind to their intracellular targets, thereby producing cells comprising intracellular target-bound RPCs;

(c) washing the product of (b) to remove unbound RPCs and produce a suspension of cells that bear (have bound to intracellular targets) a RPC;

(d) loading the suspension produced in (c) onto a microchip comprising nanoliter microwells and producing a microchip comprising nanoliter microwells that contain a single cell;

(e) covering the microchip produced in (d) with a substrate bearing a microarray comprising nucleic acid probes complementary to the nucleic acid reporter molecules of (b)(3) and arrayed in a known spatial arrangement;

(f) identifying microwells of (e) containing a single cell;

(g) maintaining the microwells that contain a single cell under conditions under which the cleavable linkers of the intracellular target-bound RPCs in the microwells are cleaved and the reporter molecules are released from the cells to which RPCs are bound to an intracellular target, and the released reporter molecules hybridize to complementary nucleic acid probes on the microarray and produce reporter molecule nucleic acid-nucleic acid probe complexes bound to the substrate;

(h) removing the substrate bearing the complexes produced in (g) from the microchip; and (i) determining whether nucleic acid-nucleic acid probe complexes are bound to the substrate, and if complexes are bound, determining that cell surface targets are present on the cell.

47. A method of multiplexed detection of intracellular targets in a pool of cells comprising:

(a) producing a suspension of fixed, permeabilized cells;

(b) incubating cells of (a) with at least two reporter-probe conjugates (RPC) each of which comprises, in the following order: (1) a nucleic acid bait that hybridizes to an intracellular target; (2) a cleavable linker; and (3) a nucleic acid reporter molecule of known sequence, under conditions under which nucleic acid bait components of the RPCs bind to their intracellular targets, thereby producing cells comprising intracellular target-bound RPCs;

(c) washing the product of (b) to remove unbound RPCs and produce a suspension of cells that bear (have bound to intracellular targets) a RPC;

(d) loading the suspension produced in (c) onto a microchip comprising nanoliter microwells and producing a microchip comprising nanoliter microwells that each contain a pool of individual cells;

(e) covering the microchip produced in (d) with a substrate bearing a microarray comprising nucleic acid probes complementary to the nucleic acid reporter molecules of (b)(3) and arrayed in a known spatial arrangement;

(f) identifying microwells of (e) that each contain a pool of individual cells;

(g) maintaining the microwells that contain a single cell under conditions under which the cleavable linkers of the intracellular target-bound RPCs in the microwells are cleaved and the reporter molecules are released from each member of the pool of individual cells to which RPCs are bound to an intracellular target, and the released reporter molecules hybridize to complementary nucleic acid probes on the microarray and produce reporter molecule nucleic acid-nucleic acid probe complexes bound to the substrate;

(h) removing the substrate bearing the complexes produced in (g) from the microchip; and (i) detecting whether nucleic acid-nucleic acid probe complexes are bound to the substrate, and if complexes are bound, determining that intracellular targets are present inside members of the pool of individual cells.

48. The method of embodiment 47, wherein the pool of cells comprises between about 2 and about 100 cells.

49. The method of embodiment 48, wherein the pool of cells comprises 2, or 3, or 4, or 5, or 6, or 7, or 8, or 9, or 10 cells.

50. The method of any one of embodiments 46 to 49, wherein the cells of (b) are incubated with 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, or 45 RPCs.

51. The method of any one of embodiments 46 to 50, wherein the nucleic acid bait of (b)(1) is between about 10 and about 500 nucleotides in length.

52. The method of any one of embodiments 46 to 51, wherein the nucleic acid bait of (b)(1) is between about 10 and about 30 nucleotides in length.

53. The method of any one of embodiments 46 to 52, wherein the nucleotide bait of (b)(1) is 10, 11, 12, 13, 14, 15, 16, 17, 18, 19, 20, 21, 22, 23, 24, 25, 26, 27, 28, 29, or 30 nucleotides in length.

54. The method of any one of embodiments 46 to 53, wherein the cleavable linker of (b)(2) is photocleavable.

55. The method of any one of embodiments 46 to 53, wherein the cleavable linker of (b)(2) is enzyme cleavable.

56. The method of any one of embodiments 46 to 55, wherein the reporter molecule of (b)(3) is between about 10 and about 500 nucleotides in length.

57. The method of any one of embodiments 46 to 56, wherein the reporter molecule of (b)(3) is between about 10 and about 30 nucleotides in length.

58. The method of any one of embodiments 46 to 57, wherein the reporter molecule of (b)(3) is 10, 11, 12, 13, 14, 15, 16, 17, 18, 19, 20, 21, 22, 23, 24, 25, 26, 27, 28, 29, or 30 nucleotides in length.

59. The method of any one of embodiments 46 to 58, wherein the microchip of (d) is made of polydimethylsiloxane (PDMS).

60. The method of any one of embodiments 46 to 59, wherein the volume of the nanoliter wells of the microchip of (d) is between about 1 nL and 999 nL.

61. The method of any one of embodiments 46 to 60, wherein the detecting of (i) is performed by microarray scanning.

62. A method of multiplexed detection of low abundance intracellular targets from an individual cell comprising:

(a) producing a suspension of fixed, permeabilized cells;

(b) incubating cells with at least two reporter-probe conjugates (RPC) each of which comprises, in the following order: (1) a nucleic acid bait that hybridizes to a low abundance intracellular target; (2) a cleavable linker; and (3) a nucleic acid reporter molecule of known sequence, under conditions under which nucleic acid bait components of the RPCs bind to their intracellular targets, thereby producing cells comprising intracellular target-bound RPCs;

(c) washing the product of (b) to remove unbound RPCs and produce a suspension of cells that bear (have bound to intracellular targets) a RPC;

(d) loading (1) the suspension produced in (c); and (2) PCR enzymes and PCR oligonucleotide primers complementary to the nucleic acid reporter molecule of (b)(3) onto a microchip comprising nanoliter microwells, thereby producing a microchip comprising nanoliter microwells that contain a single cell and PCR enzymes and oligonucleotide primers;

(e) covering the microchip produced in (d) with a substrate comprising a hydrophobic surface under conditions under which the hydrophobic surface contacts the microwells of (d);

(f) maintaining the microwells that contain a single cell and PCR enzymes and PCR oligonucleotides under conditions under which the cleavable linkers of the surface target-bound RPCs in the microwells are cleaved and the reporter molecules are released from the cells to which RPCs are bound to an intracellular target;

(g) amplifying the released nucleic acid reporter molecules of (f) by PCR, thereby producing a plurality of amplification products in each microwell;

(h) lowering the temperature inside the microwells of (g) and providing conditions under which the amplification products of (g) do not interact with the substrate of (e);

(i) maintaining the conditions of (h) and removing the substrate of (d) from the microchip;

(j) covering the microchip produced in (h) with a substrate bearing a microarray comprising nucleic acid probes complementary to the amplification products of (g) and arrayed in a known spatial arrangement;

(k) providing conditions under which the amplification products of (g) hybridize to the nucleic acid probes of (j) and produce amplification product-nucleic acid probe complexes bound to the substrate;

(l) identifying microwells of (f) containing a single cell;

(m) removing the substrate bearing the complexes produced in (k) from the microchip; and, (n) detecting whether nucleic acid-nucleic acid probe complexes are bound to the substrate, and if complexes are bound determining that intracellular targets are present.

63. A method of multiplexed detection of low abundance intracellular targets from a pool of cells comprising:

(a) producing a suspension of fixed, permeabilized cells;

(b) incubating cells with at least two reporter-probe conjugates (RPC) each of which comprises, in the following order: (1) a nucleic acid bait that hybridizes to a low abundance intracellular target; (2) a cleavable linker; and (3) a nucleic acid reporter molecule of known sequence, under conditions under which nucleic acid bait components of the RPCs bind to their intracellular targets, thereby producing cells comprising intracellular target-bound RPCs;

(c) washing the product of (b) to remove unbound RPCs and produce a suspension of cells that bear (have bound to intracellular targets) a RPC;

(d) loading (1) the suspension produced in (c); and (2) PCR enzymes and PCR oligonucleotide primers complementary to the nucleic acid reporter molecule of (b)(3) onto a microchip comprising nanoliter microwells, thereby producing a microchip comprising nanoliter microwells that each contain a pool of individual cells and PCR enzymes and oligonucleotide primers;

(e) covering the microchip produced in (d) with a substrate comprising a hydrophobic surface under conditions under which the hydrophobic surface contacts the microwells of (d);

(f) maintaining the microwells that contain a single cell and PCR enzymes and PCR oligonucleotides under conditions under which the cleavable linkers of the surface target-bound RPCs in the microwells are cleaved and the reporter molecules are released from the cells to which RPCs are bound to an intracellular target;

(g) amplifying the released nucleic acid reporter molecules of (f) by PCR, thereby producing a plurality of amplification products in each microwell;

(h) lowering the temperature inside the microwells of (g) and providing conditions under which the amplification products of (g) do not interact with the substrate of (e);

(i) maintaining the conditions of (h) and removing the substrate of (d) from the microchip;

(j) covering the microchip produced in (h) with a substrate bearing a microarray comprising nucleic acid probes complementary to the amplification products of (g) and arrayed in a known spatial arrangement;

(k) providing conditions under which the amplification products of (g) hybridize to the nucleic acid probes of (j) and produce amplification product-nucleic acid probe complexes bound to the substrate;

(l) identifying microwells of (f) each containing a pool of individual cells;

(m) removing the substrate bearing the complexes produced in (k) from the microchip; and, (n) detecting whether nucleic acid-nucleic acid probe complexes are bound to the substrate, and if complexes are bound determining that intracellular targets are present on members of the pool of individual cells.

64. The method of embodiment 63, wherein the pool of cells comprises between about 2 and about 100 cells.

65. The method of embodiment 64, wherein the pool of cells comprises 2, or 3, or 4, or 5, or 6, or 7, or 8, or 9, or 10 cells.

66. The method of any one of embodiments 62 to 65, wherein the cells of (b) are incubated with 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, or 45 RPCs.

67. The method of any one of embodiments 62 to 66, wherein the nucleic acid bait of (b)(1) is between about 10 and about 500 nucleotides in length.

68. The method of any one of embodiments 62 to 67, wherein the nucleic acid bait of (b)(1) is between about 10 and about 30 nucleotides in length.

69. The method of any one of embodiments 62 to 68, wherein the nucleotide bait of (b)(1) is 10, 11, 12, 13, 14, 15, 16, 17, 18, 19, 20, 21, 22, 23, 24, 25, 26, 27, 28, 29, or 30 nucleotides in length.

70. The method of any one of embodiments 62 to 69, wherein the cleavable linker of (b)(2) is photocleavable.

71. The method of any one of embodiments 62 to 69, wherein the cleavable linker of (b)(2) is enzyme cleavable.

72. The method of any one of embodiments 62 to 71, wherein the reporter molecule of (b)(3) is between about 10 and about 500 nucleotides in length.

73. The method of any one of embodiments 62 to 72, wherein the reporter molecule of (b)(3) is between about 10 and about 30 nucleotides in length.

74. The method of any one of embodiments 62 to 73, wherein the reporter molecule of (b)(3) is 10, 11, 12, 13, 14, 15, 16, 17, 18, 19, 20, 21, 22, 23, 24, 25, 26, 27, 28, 29, or 30 nucleotides in length.

75. The method of any one of embodiments 62 to 74, wherein the microchip of (d) is made of polydimethylsiloxane (PDMS).

76. The method of any one of embodiments 62 to 75, wherein the volume of the nanoliter wells of the microchip of (d) is between about 1 nL and 999 nL.

77. The method of any one of embodiments 62 to 76, wherein the detecting of (n) is performed by microarray scanning.

78. The method of any one of embodiments 62 to 77, wherein the substrate of (e) is glass.

79. The method of any one of embodiments 62 to 78, wherein the hydrophobic surface of the substrate of (e) is Teflon®.

80. The method of any one of embodiments 62 to 78, wherein the hydrophobic surface of the substrate of (e) is alkane chain functionalized silicone oxide or metal surfaces.

81. The method of any one of embodiments 62 to 80, wherein the temperature is lowered below 0° C.

82. The method of embodiment 81, wherein the temperature is lowered below −10° C. 83. The method of any one of embodiments 62 to 82, wherein the temperature is lowered by between about 20° C. and 100° C.

84. The method of any one of embodiments 62 to 83, wherein the temperature is lowered over a time span of 1 ms to 5 minutes.

85. The method of embodiment 84, wherein the temperature is lowered over a time span of 0.5 ms to 2 minutes.

86. The method of embodiment 85, wherein the temperature is lowered over a time span of 1 s to 1 minute.

87. A method of multiplexed detection of intracellular targets comprising:

(a) incubating a suspension of fixed, permeabilized cells with at least two reporter-probe conjugates (RPC) each of which comprises, in the following order: (1) a nucleic acid bait that hybridizes to an intracellular target; (2) a cleavable linker; and (3) a nucleic acid reporter molecule of known sequence, under conditions under which nucleic acid bait components of the RPCs bind to their intracellular targets, thereby producing cells comprising intracellular target-bound RPCs;

(b) loading the suspension produced in (a) onto a microchip comprising a plurality of nanoliter microwells to produce a loaded microchip;

(c) contacting the loaded microchip produced in (b) and a substrate bearing a microarray comprising a plurality of capture probes, wherein each capture probe comprises a nucleic acid sequence complementary to at least one of the nucleic acid reporter molecules of (b)(3), wherein the plurality of capture probes is arrayed on the substrate in a known spatial arrangement, wherein contacting of the microchip and the substrate encloses each microwell of the microchip and wherein each enclosed microwell contains each capture probe of the microarray;

(d) maintaining the loaded microchip under conditions under which the cleavable linkers of the intracellular target-bound RPCs in the microwells are cleaved and the reporter molecules are released from the cells to which RPCs are bound to an intracellular target, and the released reporter molecules hybridize to complementary nucleic acid probes on the microarray and produce reporter molecule—capture probe complexes bound to the substrate;

(e) removing the substrate bearing the complexes produced in (d) from the microchip; and (f) visualizing one or more reporter molecule—capture probe complexes bound to the substrate and (g) identifying one or more intracellular targets corresponding to one or more reporter molecules bound to the substrate for at least one enclosed microwell containing less than five cells.

88. The method of embodiment 87, wherein the method comprises identifying one or more corresponding intracellular targets present on the substrate for at least one enclosed microwell containing a single cell.

89. The method of embodiment 87 or 88, wherein the method comprises incubating a suspension of fixed, permeabilized cells with at least 5 RPC, at least 10 RPC, at least 15 RPC, at least 20 RPC, at least 25 RPC, at least 30 RPC, at least 35 RPC, at least 40 RPC, at least 45 RPC, or at least 50 RPC.

90. The method of any one of embodiments 87-89, wherein the microchip comprises between 2 and 20,000 microwells, inclusive of the endpoints.

91. The method of any one of embodiments 87-89, wherein the microchip comprises between 5,000 and 20,000 microwells, inclusive of the endpoints.

92. The method of any one of embodiments 87-91, wherein each microwell has a volume of between 1 nanoliter and 999 nanoliters.

93. The method of any one of embodiments 87-91, wherein each microwell has a volume of between 1 nanoliter and 10 nanoliters.

94. The method of any one of embodiments 87-93, wherein each microwell comprises a volume of the suspension of (a) of between 1 nanoliter and 10 nanoliters.

95. The method of any one of embodiments 87-94, wherein the nucleic acid bait of (a)(1) comprises a DNA sequence, an RNA sequence, a peptide or a combination thereof.

96. The method of any one of embodiments 87-95, wherein the nucleic acid reporter molecule of (a)(3) comprises a DNA sequence, an RNA sequence, a peptide or a combination thereof.

97. The method of any one of embodiments 87-95, wherein the nucleic acid reporter molecule of (a)(3) comprises a DNA sequence, an RNA sequence, a peptide or a combination thereof.

98. The method of any one of embodiments 87-95, wherein the nucleic acid reporter molecule of (a)(3) comprises a DNA sequence.

99. The method of any one of embodiments 87-98, wherein the substrate comprises a glass composition.

100. The method of any one of embodiments 87-99, wherein the nucleic acid sequence complementary to at least one of the nucleic acid reporter molecules of (b)(3) of each capture probe comprises a DNA sequence, an RNA sequence, a peptide or a combination thereof.

101. The method of any one of embodiments 87-99, wherein the nucleic acid sequence complementary to at least one of the nucleic acid reporter molecules of (b)(3) of each capture probe comprises a DNA sequence.

102. The method of any one of embodiments 87-101, wherein the plurality of capture probes comprises a number of distinct capture probes equal to the number of RPCs of (a).

103. The method of any one of embodiments 87-101, wherein the plurality of capture probes comprises at least 2, at least 5, at least 10, at least 15, at least 20, at least 25, at least 30, at least 35, at least 40, at least 45, or at least 50 capture probes.

104. The method of any one of embodiments 87-103, wherein the known spatial arrangement of capture probes of the microarray comprises a repeating pattern.

105. The method of embodiment 104, wherein the repeating pattern comprises parallel lines.

106. The method of any one of embodiments 87-105, wherein the enclosed microwells are prevented from fluid communication with any other enclosed microwell on the microchip.

107. The method of embodiment 106, wherein the substrate contacts the entire surface of the microchip, enclosing each microwell of the microchip.

108. The method of any one of embodiments 87-107, wherein each capture probe of the plurality of capture probes comprises a detectable label.

109. The method of embodiment 108, wherein the detectable label is a fluorescent label.

110. The method of any one of embodiments 108-109, wherein the identifying step comprises combining a signal from the detectable label and a position within the known spatial arrangement within the microarray to determine an identity of the reporter molecule—capture probe complex bound to the substrate.

111. The method of any one of embodiments 87-110, further comprising the step of washing the product of (a) to remove unbound RPCs and produce a suspension of cells that comprise a RPC.

112. The method of any one of embodiments 87-111, wherein the cleavable linker of (a)(2) is photocleavable.

113. The method of any one of embodiments 87-111, wherein the cleavable linker of (a)(2) is enzyme cleavable.

114. The method of any one of embodiments 87-113, wherein the microchip is made of polydimethylsiloxane (PDMS).

115. The method of any one of embodiments 87-115, wherein the visualizing step is performed by microarray scanning.

116. The method of any one of embodiments 87-116, wherein one or more intracellular targets are low abundance and wherein the method further comprises incubating the suspension of (a) with PCR enzymes and PCR oligonucleotide primers complementary to the nucleic acid reporter molecule of (a)(3) to produce a PCR suspension,
loading onto the microchip the PCR suspension to produce a PCR loaded microchip;
maintaining the PCR loaded microchip under conditions under which the cleavable linkers of the intracellular RPCs in the microwells are cleaved and the reporter molecules are released from the cells to which RPCs are bound to an intracellular target;
amplifying the released nucleic acid reporter molecules of by PCR, thereby producing a plurality of amplification products in each microwell;
contacting the PCR loaded microchip with a substrate bearing a microarray comprising nucleic acid probes complementary to the amplification products.

117. The method of embodiment 116, wherein the method further comprises contacting the PCT loaded microchip with a substrate comprising a hydrophobic surface and providing conditions under which the amplification products do not interact with the hydrophobic surface prior to contacting the PCR loaded microchip with a substrate bearing a microarray comprising nucleic acid probes complementary to the amplification products.

118. The method of embodiment 117, further comprising lowering at temperature within each of the microwells prior to contacting the PCT loaded microchip with a substrate comprising a hydrophobic surface.

119. The method of embodiment 117 or 118, wherein the hydrophobic surface of the substrate is Teflon®.

120. The method of embodiment 117 or 118, wherein the hydrophobic surface of the substrate of (e) is alkane chain functionalized silicone oxide or metal surfaces.

121. The method of embodiment 118, wherein the temperature is lowered below 0° C.

122. The method of embodiment 118, wherein the temperature is lowered below −10° C.

123. The method of embodiment 118, wherein the temperature is lowered by between about 20° C. and 100° C.

124. The method of any one of embodiments 118 or 121-123, wherein the temperature is lowered over a time span of 1 millisecond to 5 minutes.

125. The method of any one of embodiments 118 or 121-123, wherein the temperature is lowered over a time span of 0.5 millisecond to 2 minutes.

126. The method of any one of embodiments 118 or 121-123, wherein the temperature is lowered over a time span of 1 second to 1 minute.

The following examples are meant to illustrate, but in no way to limit, the claimed invention.

EXAMPLES

Example 1: Materials and Methods

I. Assay procedure (using miRNA detection as an example)
1. Spin down harvested cells and wash them with DPBS twice
2. Fix cells with paraformaldehyde solution (4% in PBS) inside the tube. Incubate cells for 10 min at 37° C.
3. After 10 min, put the cells on ice for 1 min and then spin them down to remove paraformaldehyde solution
4. Add 90% methanol into the cells and leave them on ice for 30 min.
5. After half an hour, spin down the cells and remove methanol solution.
6. Add blocking buffer (3% BSA+2% NaCl in TET) inside the tube and incubate cells at 37° C. for 1 hour.
7. After an hour, the cells were spin down and blocking buffer was removed.
8. Solution A (T4 DNA ligase inside NEB2A and TET) should be added to the cells
9. Add 1 uL PC linker conjugated micro RNA probe solution (1 ul*100 uM=100 nmole) to 1 mL cell suspension and incubated it at 37° C. for 2 hours.
   At the same time, the glass slide with DNA probe should be blocked with the Blocking buffer for 2 hours.
1. After 2 hours, cells should be spin down and supernatant was removed. Wash the cells thoroughly with TET six times (incubation step is needed in each washing step).
10. Re-suspend the cells in another 1 mL solution A. Then pipette 200 uL cell suspension onto the PDMS microwells and put the glass slide with flow patterned DNA probes on top of it with surface with DNA facing down. Clamp the glass slide and PDMS microwell slab together.
11. Scan the PDMS microwells trapped with cells using dark field and oblique channel respectively.
12. Flood the device with UV lamp for 900 s (15 min)
13. Put the device into the incubator (37° C.) overnight
14. Remove the device from incubator and then release the glass slide from PDMS microwell slab
15. Wash the glass slide with 5% BSA solution several times
16. Dilute SA-PE 1:100 in 5% BSA and use pipette to add 200 uL onto the glass slide and incubate for 30 min.
17. Wash the glass slide several times and dip it sequentially into DPBS, 50/50 DPBS/water, DI water. Blow dry the slide and detect the signal with Genepix fluorescence scanner.

Example 2: Schematic Depiction of Multiplexed Identification of Intracellular Targets from an Individual Cell FIG. 1 depicts a schematic depiction of some embodiments of the multiplexed detecting of intracellular targets from an individual cell. In this non-limiting embodiment, miRNA capture strands serve as nucleic acid bait of the reporter-probe conjugates (RPCs).

In this embodiment, the method of multiplexed detection of intracellular targets in an individual cell comprises (a) producing a suspension of fixed, permeabilized cells, (b) incubating cells of (a) with at least two reporter-probe conjugates (RPC) each of which comprises, in the following order: (1) a nucleic acid bait (FIG. 1, any of the miRNA 1-3)

that hybridizes to an intracellular target or a cell surface target; (2) a cleavable linker; and (3) a nucleic acid reporter molecule of known sequence (FIG. 1 A, B or C), under conditions under which nucleic acid bait component of the RPCs bind to their intracellular targets, thereby producing cells comprising target-bound RPCs, (c) washing the product of (b) to remove unbound RPCs and produce a suspension of cells containing target-bound RPCs, (d) loading the suspension produced in (c) onto a microchip comprising nanoliter microwells and producing a microchip comprising nanoliter microwells that contain a single cell, (e) covering the microchip produced in (d) with a substrate bearing a microarray comprising nucleic acid probes complementary to the nucleic acid reporter molecules of (b)(3) and arrayed in a known spatial arrangement (FIG. 1, A', B' or C'), (f) identifying microwells of (e) containing a single cell, (g) providing conditions under which the cleavable linkers of the target-bound RPCs in the microwells of (f) are cleaved, releasing the reporter molecule from the target-bound bait, under conditions under which nucleic acid reporter molecules of the RPCs hybridize to complementary nucleic acid probes on the microarray and produce reporter molecule nucleic acid-nucleic acid probe complexes bound to the substrate, (h) removing the substrate bearing the complexes produced in (g) from the microchip, and (i) detecting the location of nucleic acid-nucleic acid probe complexes bound to the substrate and determining if intracellular targets are present.

The identity of the intracellular target (miRNA 1, 2 or 3) is determined with reference to the position of the complementary nucleic acid on the microarray (A-A', B-B' or C-C'), which specifies the target identity. For example, the detection of A-A' on the microarray indicates the presence of miRNA-1 inside the cell.

Example 3: Schematic Depiction of an Alternative Embodiment of Multiplexed Identification of Intracellular Targets from an Individual Cell FIG. 2 depicts another non-limiting embodiment of the instant disclosure. This embodiment follows the same general method as the embodiment described in Example 2, however the capture portion of the RPC comprises an antibody that binds to an intracellular target rather than a nucleic acid bait sequence.

Figure 3:
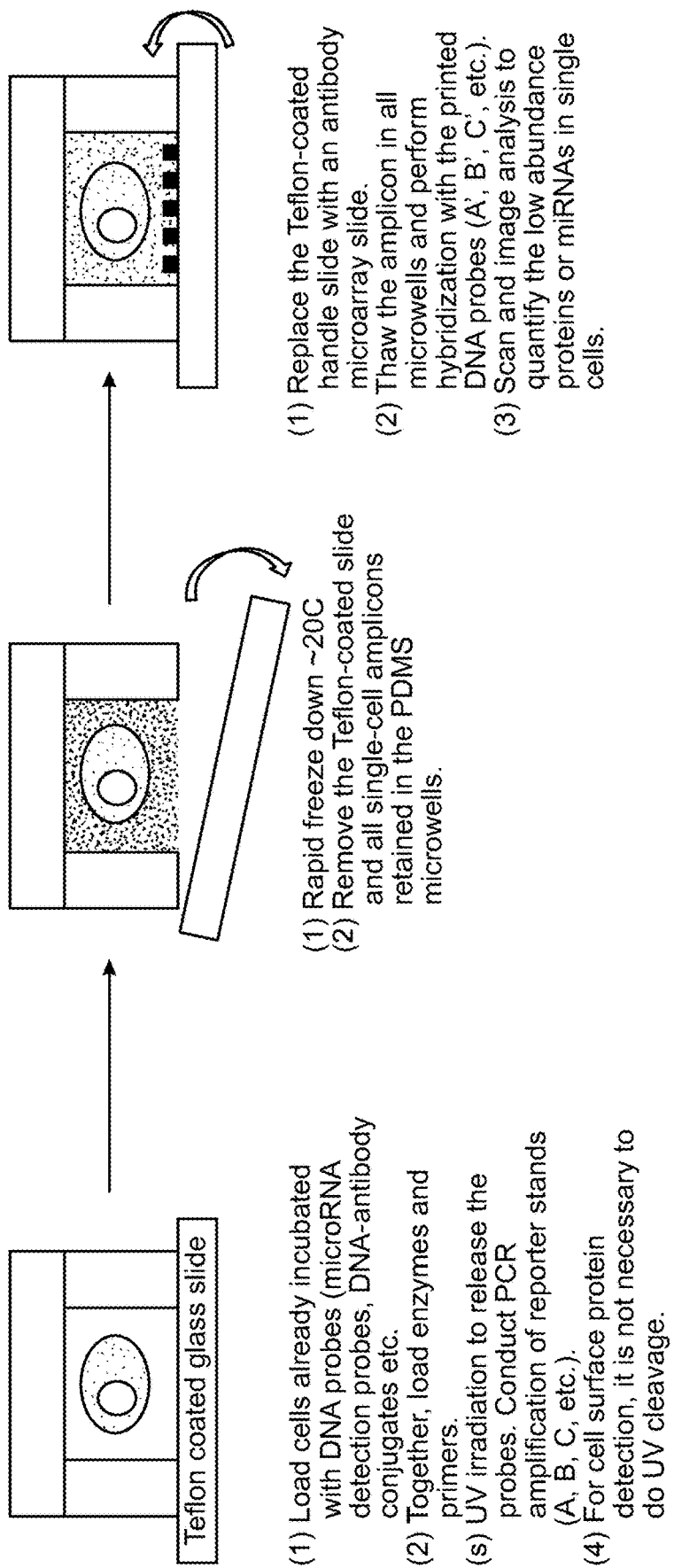
FIG. 3 is a schematic representation of some embodiments of a method for multiplex detection of low abundance targets from an individual cell that enables on-chip individual-cell multiplex PCR coupled with high-density DNA microarray to detect a panel of molecular targets.

Example 4: Schematic Depiction of Multiplexed Identification of Low Abundance Targets from an Individual Cell FIG. 3 depicts several steps of some embodiments of the multiplexed identification of low abundance targets from a single cell. After the cells comprising target-bound RPCs have been loaded into microwells with PCR enzymes and primers, PCR is performed under conditions under which the cleaved nucleic acid reporter molecules of the RPCs are amplified, thereby producing a plurality of PCR amplicons in each microwell. The temperature inside the microwells is then rapidly lowered, providing conditions under which the PCR amplicons are repelled from the Teflon® surface of the substrate covering the microwells. The substrate is then removed and the microchip is covered with a substrate bearing a microarray comprising nucleic acid probes complementary to the PCR amplicons and arrayed in a known spatial arrangement. The process then proceeds as in Example 2, step (f).

Example 5

Figure 4:
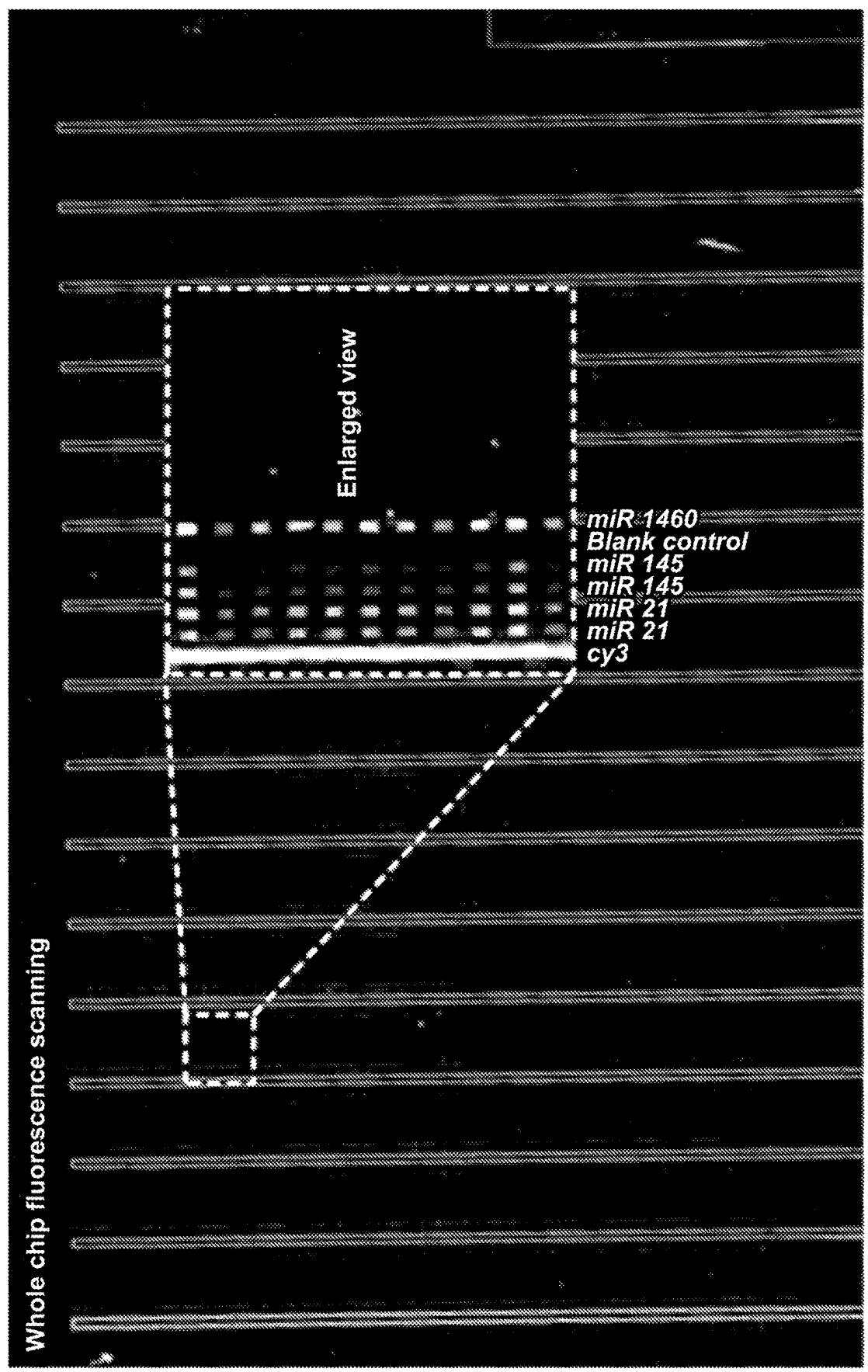
FIG. 4 is a microarray scanner image showing the entire DNA microarray slide used to detect multiple miRNAs at the single cell level. Enlarged view shows excellent signal to background ratio.

FIG. 4 shows a representative scanner image showing the entire DNA microarray slide used to detect multiple miRNAs at the single cell level. Enlarged view shows excellent signal to background ratio.

Figure 5:
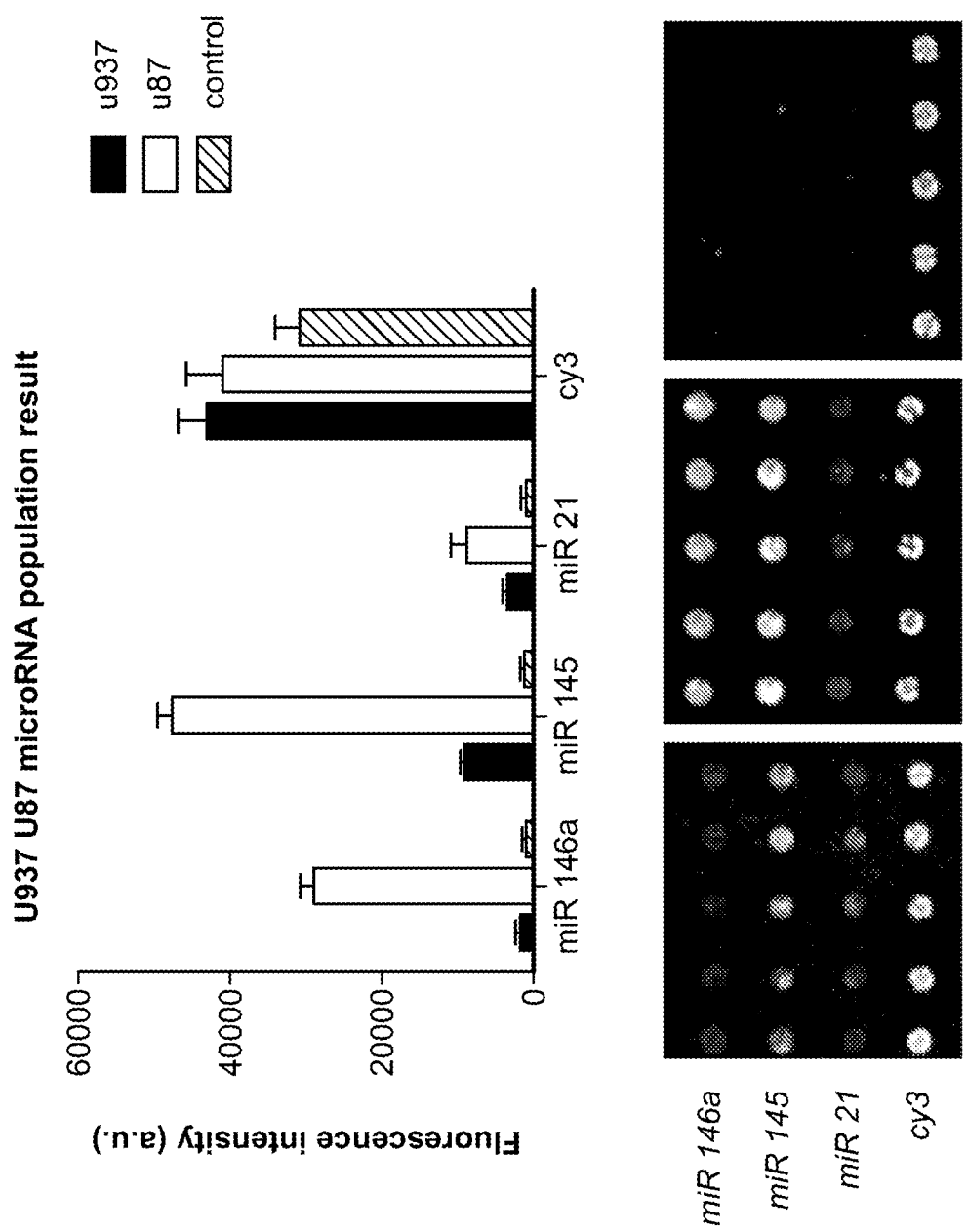
FIG. 5 shows quantification of multiple miRNAs detected using the scheme described in FIG. 1. Target miRNA levels in two cell lines (U937 and U87) were measured.
Figure 6:
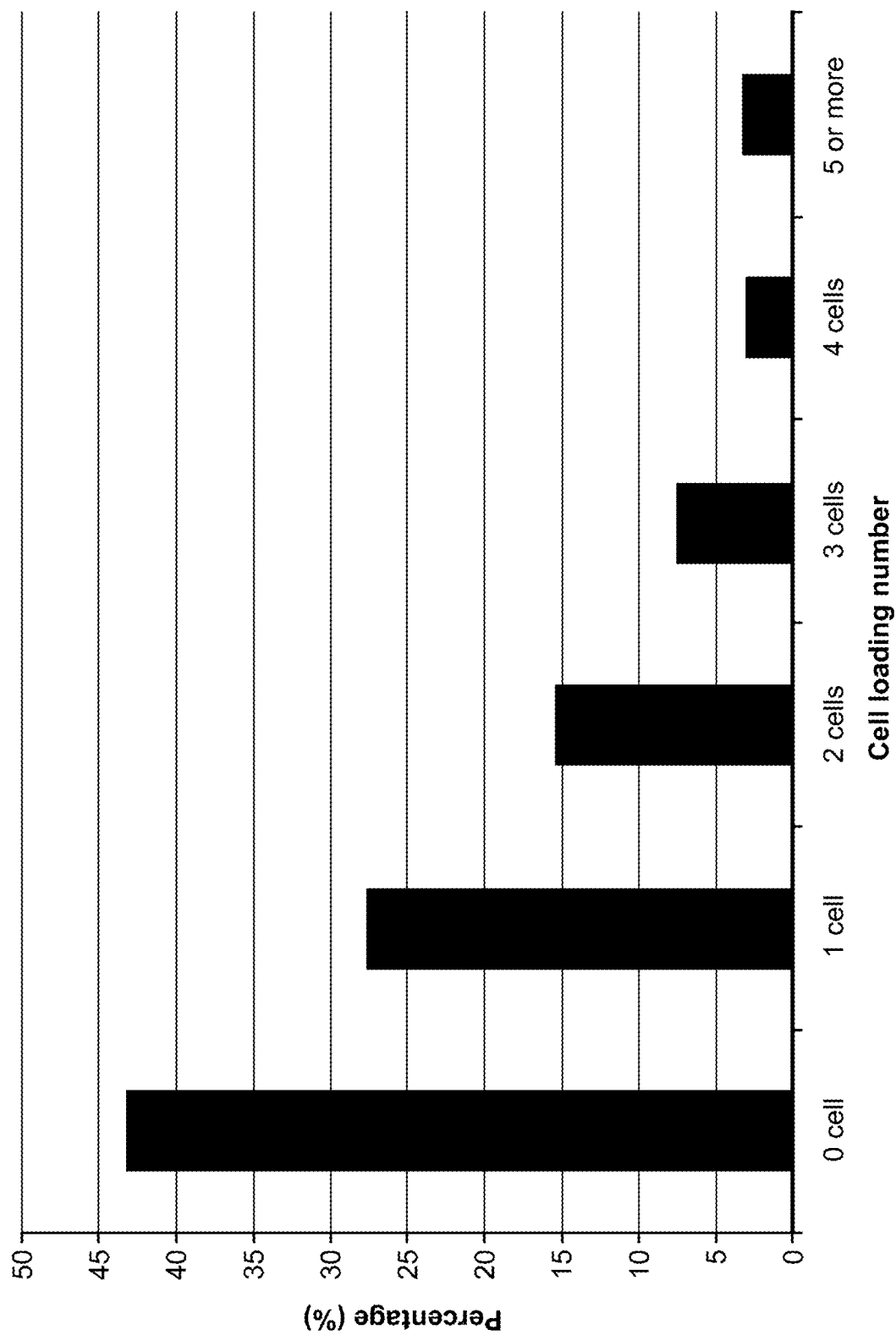
FIG. 6 is a histogram depicting an example of cell loading per microwell. In some embodiments, each microwell contains 5,000-20,000 microwells. According to the methods of the disclosure, and as shown in this example, cells may be dispensed directly to the surface of the microchip and allowed to settle in at least one (one or more) of the microwells therein. The cells may be trapped within the microwell(s) by placing a cover substrate (e.g., a glass slide) on top of the microchip to enclose the microwell(s) (which may also seal the microwell(s)). This plot shows a histogram of cell loading per microwell. Cell loading is expressed as a percentage of microwell containing 0, at least 1, at least 2, at least 3, at least 4, or at least 5 cells within a single microchip. In some embodiments, 25-33% (e.g., 25%, 30% or 33%) of the microwells within a single microchip contain only a single cell. In some embodiments, more than 30% or more than 50% of the microwells within a single microchip contain only a single cell.

FIG. 5 shows quantification of multiple miRNAs detected using the scheme depicted in FIG. 1. Two cell lines (U937 and U87) were measured.

Example 6

Figure 7:
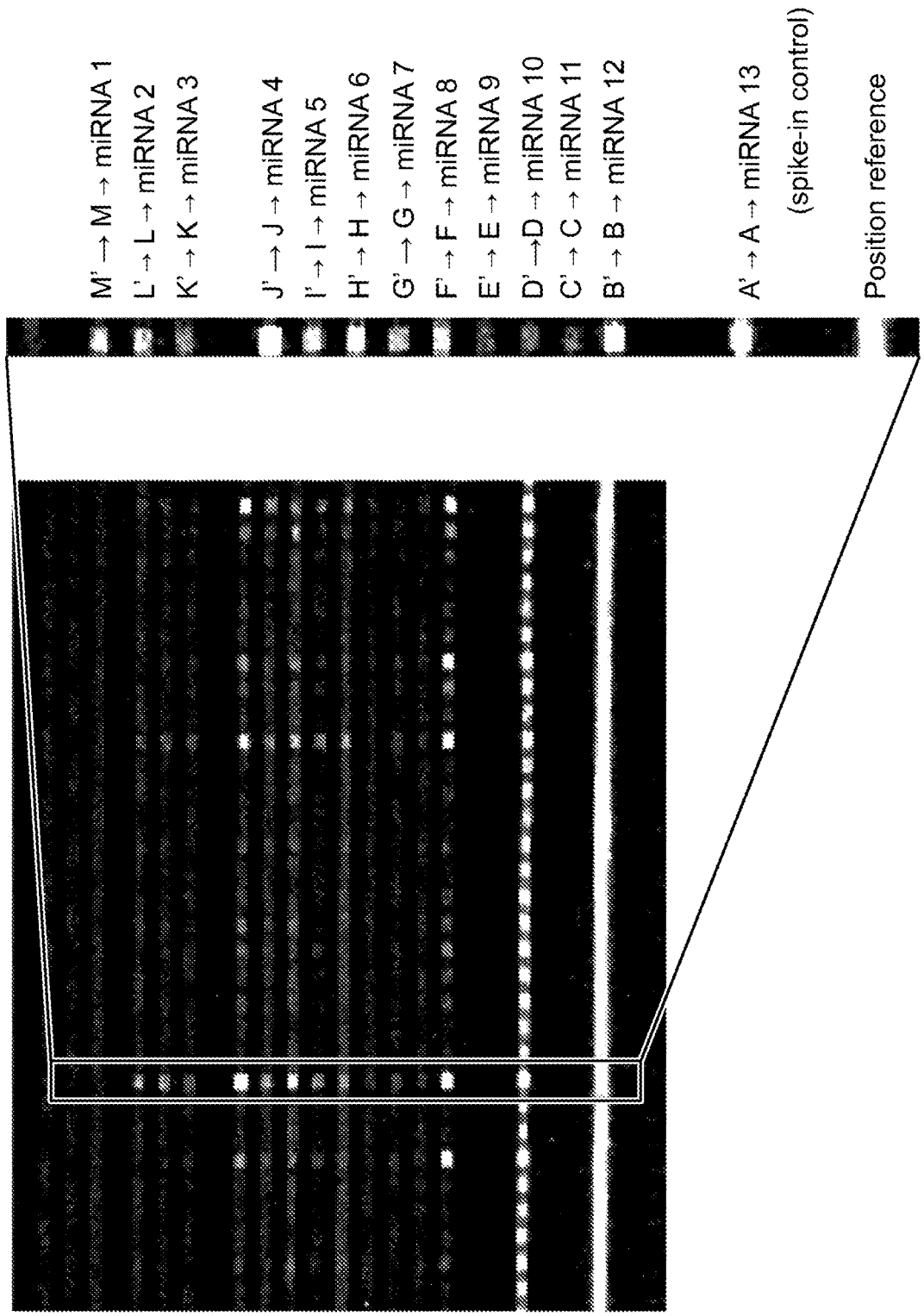
FIG. 7 is a scanner fluorescence image depicting the results of an analysis of single cells using a panel of 13 miRNA biomarkers.

Capture probes comprising DNA strands (FIG. 7, A'-M') were immobilized on the substrate as a set of parallel lines that are oriented such that each microwell intersects the full set of DNA oligomers (A'-M') (i.e., each microwell intersects each of the 13 miRNA biomarkers in the panel). Reporter strands comprising fluorescent, Cy3-labelled DNA strands (A-M), are released from the trapped cells, immobilized onto the substrate by the capture probes and detected/imaged/visualized using a fluorescence microarray scanner. The signal intensity from the reporter strands (FIG. 7, A-M) hybridized to the immobilized capture strands (FIG. 7, A'-M') may be used to determine an abundance of each of the corresponding miRNAs in the single cell trapped within each of the microwells of the microchip. Tables 1 and 2 provide the sequences of the capture and reporter DNA strands (FIG. 7, A-M, A'-M') for detecting the corresponding miRNAs. The cells shown in FIG. 7 are from the human THP-1 cell line.

Example 7

Figure 8:
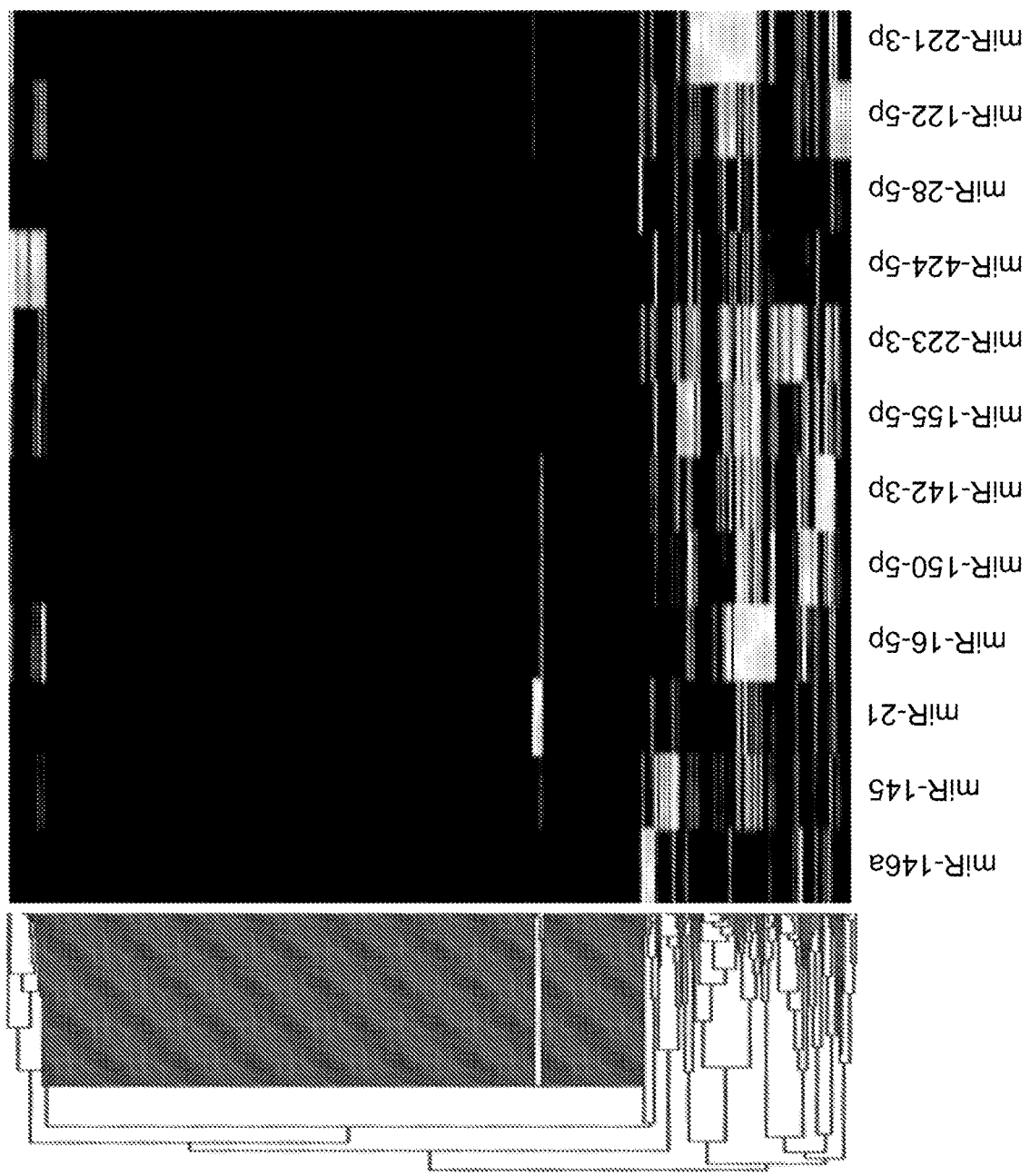
FIG. 8 is a heatmap showing examples of single-cell miRNA profiles. Each column indicates a specific miRNA detected and each row across the heatmap represents a single cell.

In this example, approximately 1000 single cells were measured on a microchip. Non-supervised clustering was performed to group the cells. FIG. 8 is a heatmap showing single-cell miRNA profiles. Each column indicates a specific miRNA detected and each row across the heatmap is a single cell. The cells shown in this FIG. 8 are from the human THP-1 cell line.

Example 8

Figure 9A:
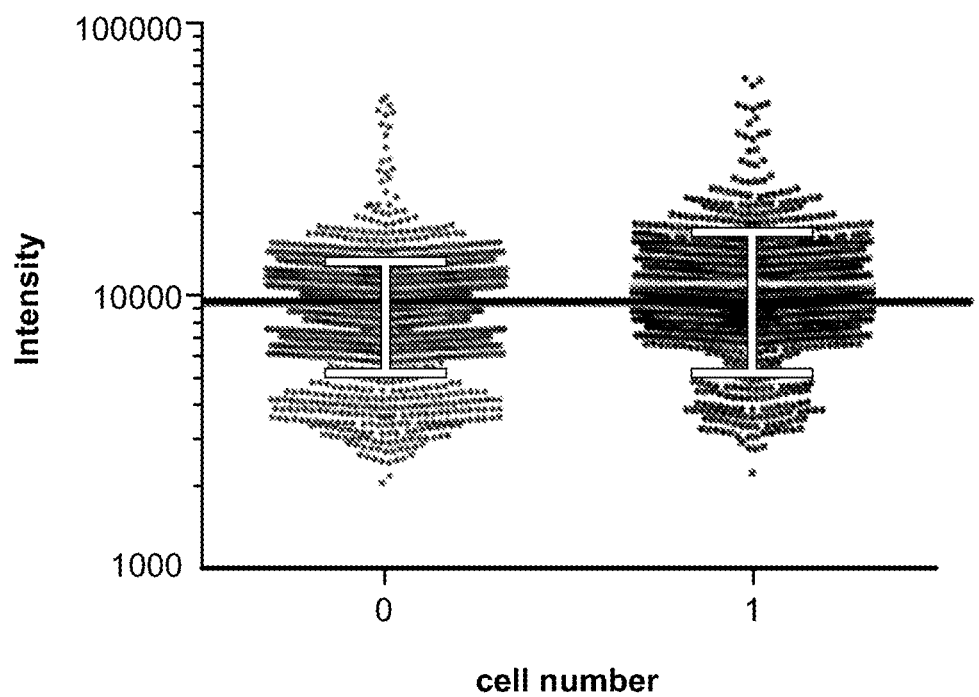
FIG. 9A is a graph depicting capture and detection of miR-16-5p from single cells. A log-scale scatter plot shows the fluorescence intensity distribution in zero cell and single cell microwells. The bars show average and standard deviation.
Figure 9B:
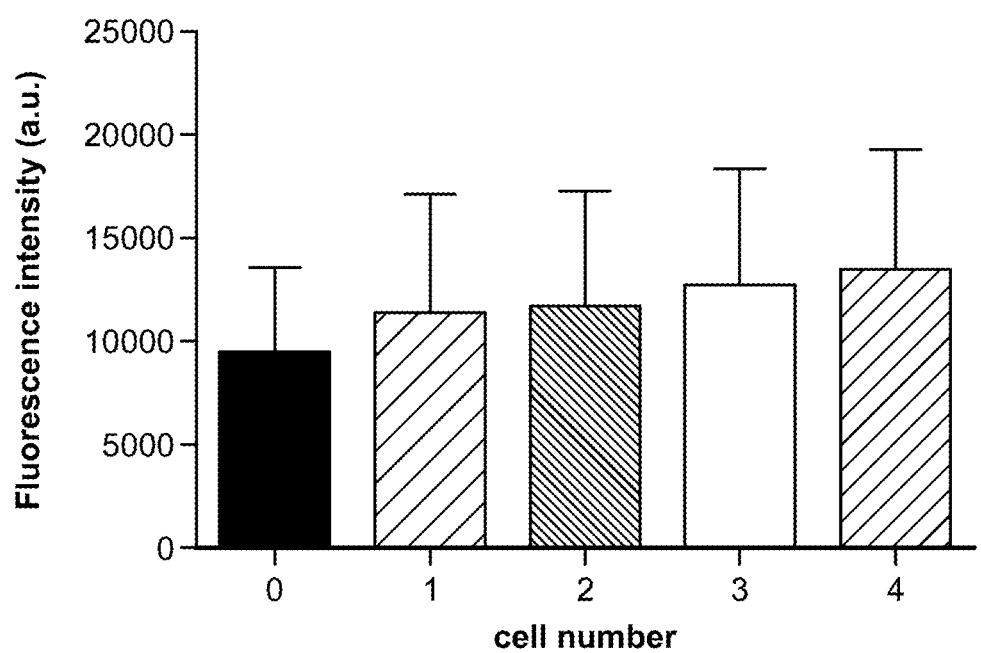
FIG. 9B is a graph depicting capture and detection of miR-16-5p from single cells. This is a log-scale raw intensity average over all zero cell microwells compared to single, 2, 3, and 4 microwells, respectively. The zero cell microwell average can be used as background to calculate the net signals in single and multiple cell microwells.

This example demonstrates capture and detection of miR-16-5p from single cells. A log-scale scatter plot shows the fluorescence intensity distribution in zero cell and single cell microwells (FIG. 9). A graph shows log-scale raw intensity average over all zero cell microwells compared to single, 2, 3, and 4 microwells, respectively is shown (FIG. 9B). The zero cell microwell average can be used as background to calculate the net signals in single and multiple cell microwells.

Example 9

Figure 10A:
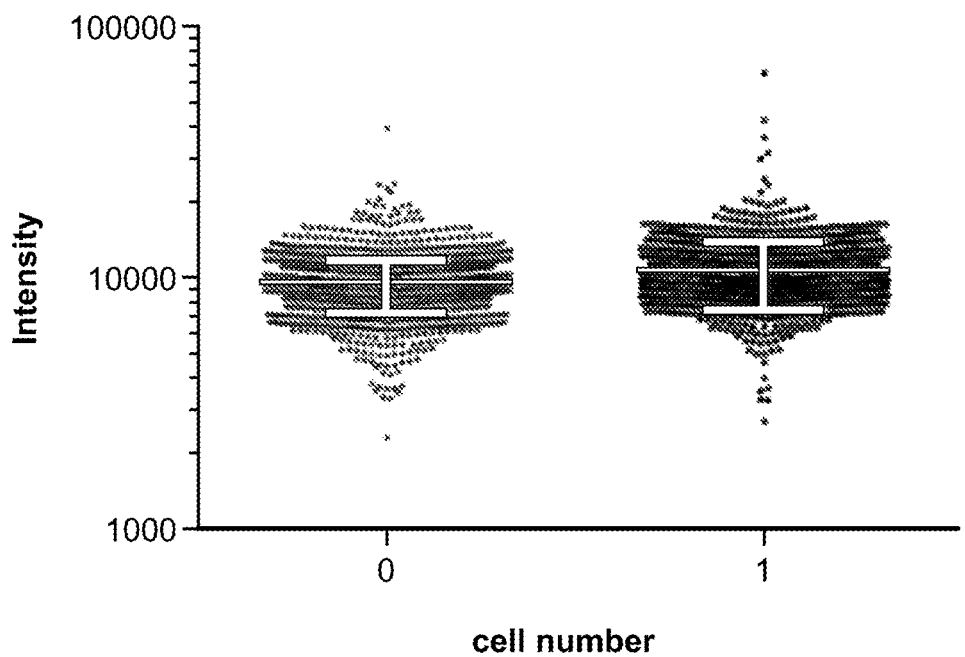
FIG. 10A is a graph depicting capture and detection of miR-223-3p in single cells. This is a log-scale scatter plot showing the fluorescence intensity distribution in zero cell and single cell microwells. The bars show average and standard deviation.
Figure 10B:
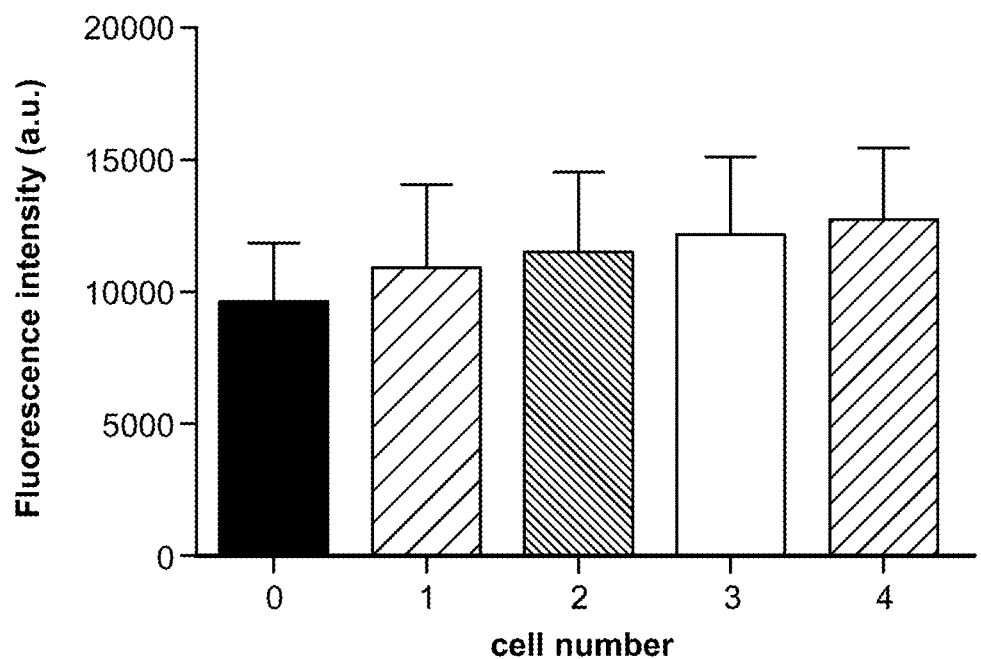
FIG. 10B is a graph depicting capture and detection of miR-223-3p in single cells. This is a log-scale raw intensity average over all zero cell microwells compared to single, 2, 3, and 4 microwells, respectively. The zero cell microwell average can be used as background to calculate the net signals in single and multiple cell microwells.

This example demonstrates capture and detection of miR-223-3p in single cells. A log-scale scatter plot shows the fluorescence intensity distribution in zero cell and single cell microwells (FIG. 10A). A graph shows a log-scale raw intensity average over all zero cell microwells compared to single, 2, 3, and 4 microwells, respectively (FIG. 10B). The zero cell microwell average can be used as background to calculate the net signals in single and multiple cell microwells.

Example 10

Figure 11:
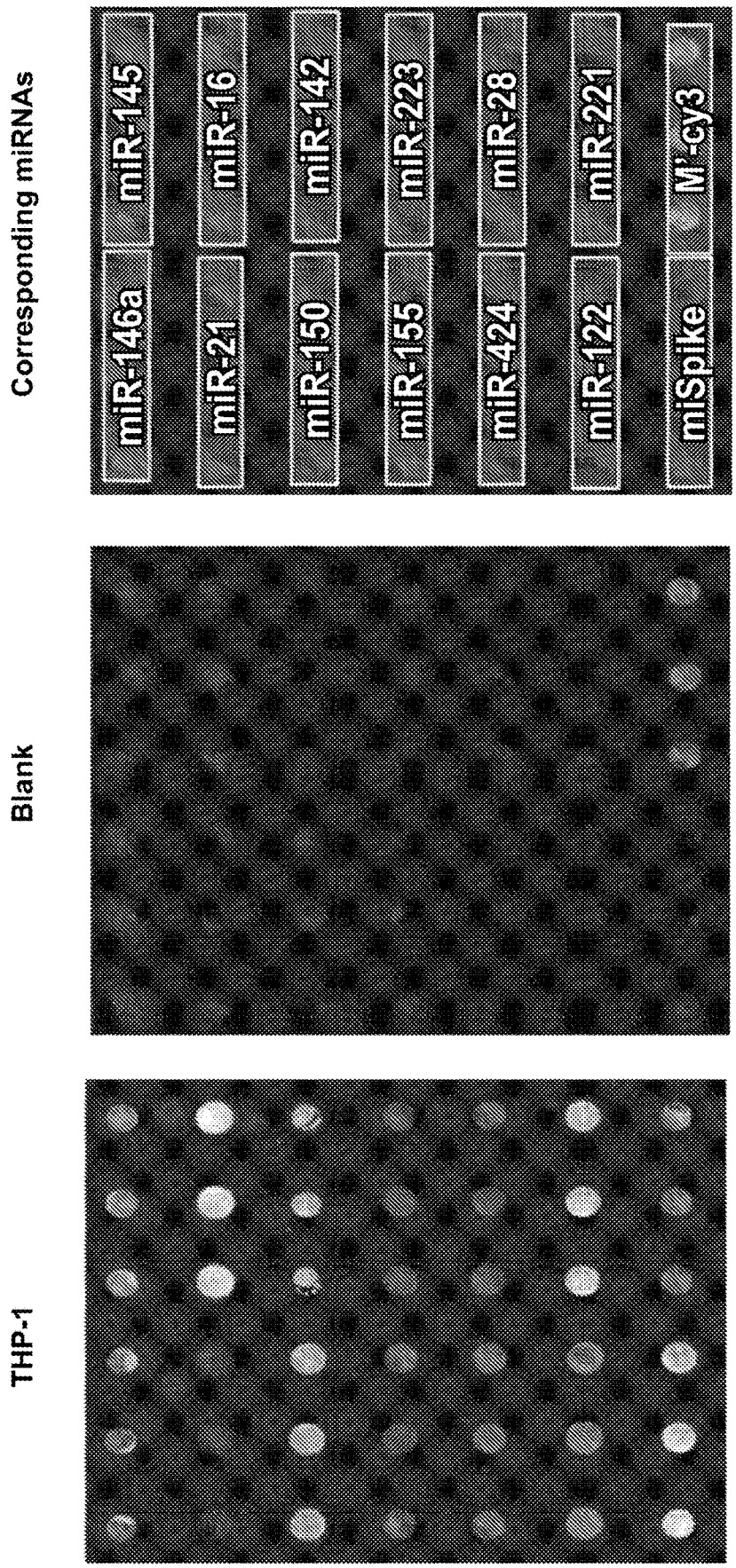
FIG. 11 is a series of images depicting a validation of the results shown in FIGS. 6-10 using the standard method of bulk miRNA detection (a pin-spotted microarray). The left panel is an image showing the result of bulk miRNA detection. The middle image was obtained by adding deionized water to a capture DNA microarray spotted in the same format as the left panel. The right panel is a schematic showing the layout of corresponding miRNAs detected in triplicate using this approach. The results from the pin-spotted microarray are in agreement with single-cell averages shown in FIGS. 6-10.
Figure 12:
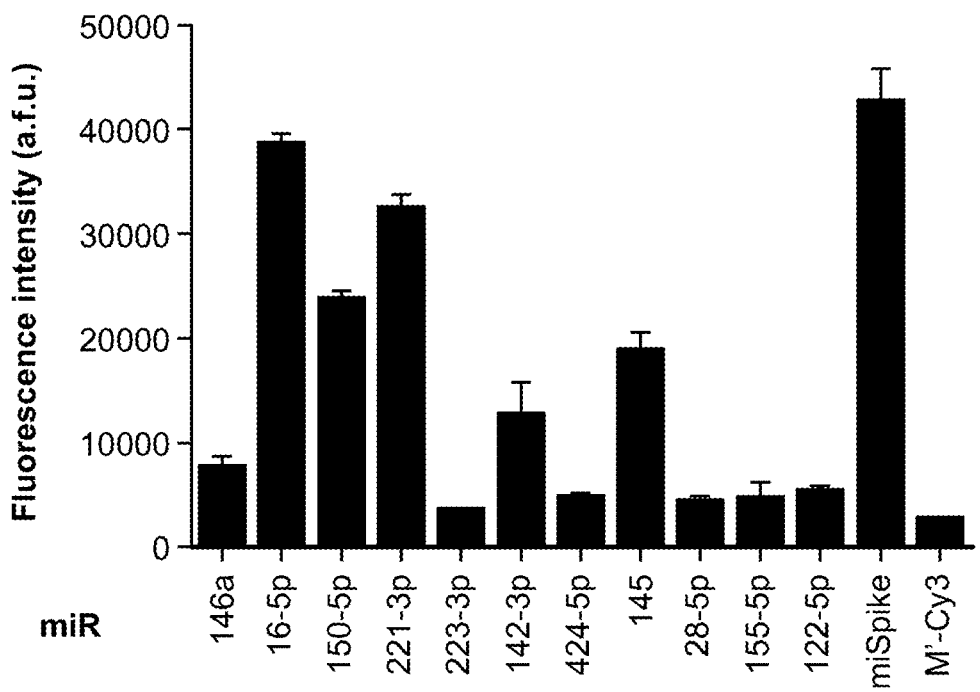
FIG. 12 is a graph depicting the fluorescence intensity averaged over three spots for each miRNA (as shown in FIG. 11, left and right panels) and the standard deviation. The results from the pin-spotted microarray are in agreement with single-cell averages shown in FIGS. 6-10.

The standard method of bulk miRNA detection (a pin-spotted microarray) was performed. A series of images depicting a validation of the results shown in FIGS. 6-10 is shown in FIG. 11. The same cell line THP-1 was used in this example as in the studies depicted in FIGS. 6-10. Cells were fixed, permeabilized, incubated with miRNA capture/DNA report conjugates, and induced to release reporter strands (A-M) (by UV exposure) according to the same methods and procedures that were used for the studies depicted in FIGS. 6-10. However, in a departure from the studies described in FIGS. 6-10, the cells were spun down and the supernatant containing released reporter strands was applied to a pin-spotted microarray made of the same set of capture DNA probes (A'-M'). The results from the pin-spotted microarray are in good agreement with single-cell averages shown in FIGS. 6-10.

Example 11

Figure 13:
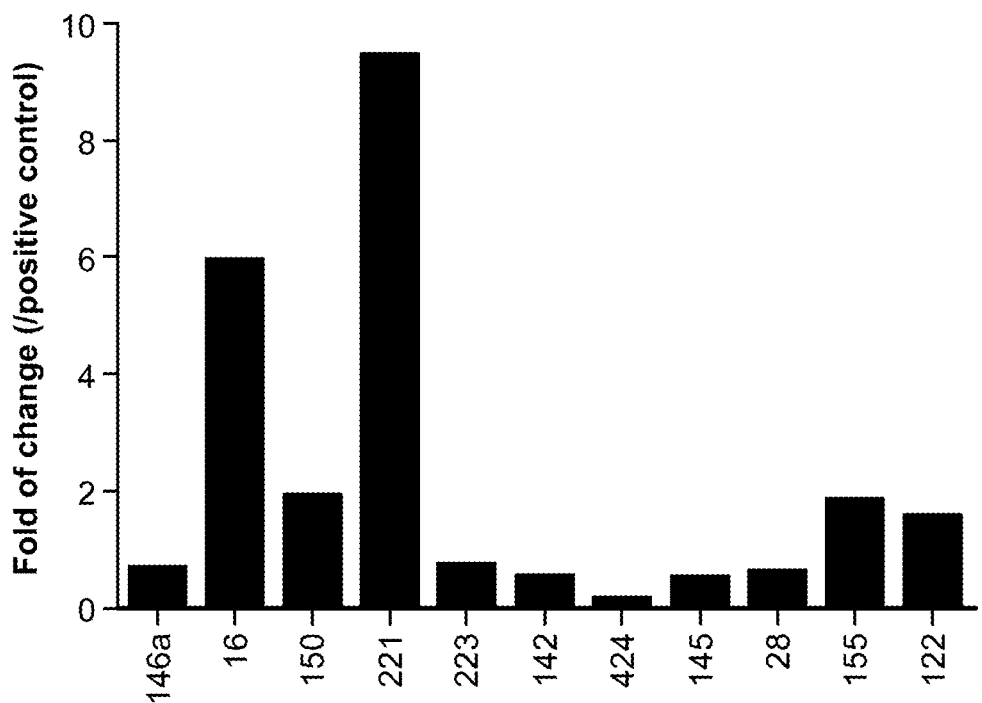
FIG. 13 is a graph depicting validation of the single cell assay of the disclosure via the standard quantitative PCR (qPCR) assay.

The example validates the single cell assay of the disclosure via the standard quantitative PCR (qPCR) assay. THP-1 cells (approximately 1 million cells) were lysed using QIAGEN® RNeasy kit, and miRNAs released from the bulk sample (as described in FIG. 11) were detected using standard qPCR. For the most abundant miRNAs (miR16, miR221, and miR150), the levels of each of these miRNA detected by standard qPCR are the same as the levels of each of these miRNA detected by the methods of the disclosure (FIG. 13). Differences between these methods include miR145 and miR155. MiR145 was detected by the methods of the disclosure, but not qPCR. MiR155 was detected by qPCR but not with the methods of the disclosure, due in part to the difference in miRNA processing. According to the methods of the disclosure, miRNAs remain bound to Ago proteins and a portion of the sequence may not be accessible to miRNA capture sequence. In the standard qPCR, miRNAs were fully stripped off from Ago proteins and may be subjected to rapid degradation. Thus, miRNAs analyzed by qPCR versus the methods of the disclosure may have different degradation mechanisms and rates.

Example 12

Figure 14A:
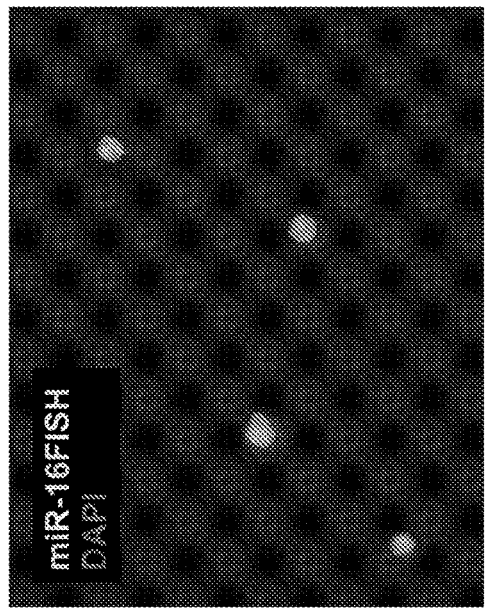
FIGS. 14A-14C show a pair of photographs depicting validation of the single cell assay of the disclosure for detecting miR16 using fluorescence in situ hybridization (FISH) and a quantification of the fluorescence intensity in each of FIG. 14A and FIG. 14B.
Figure 14B:
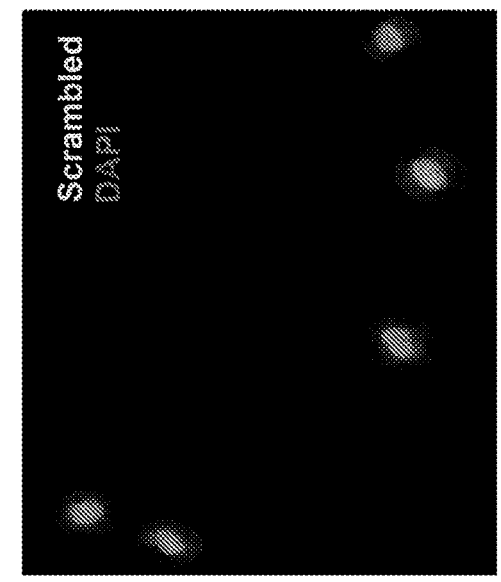
Figure 14C:
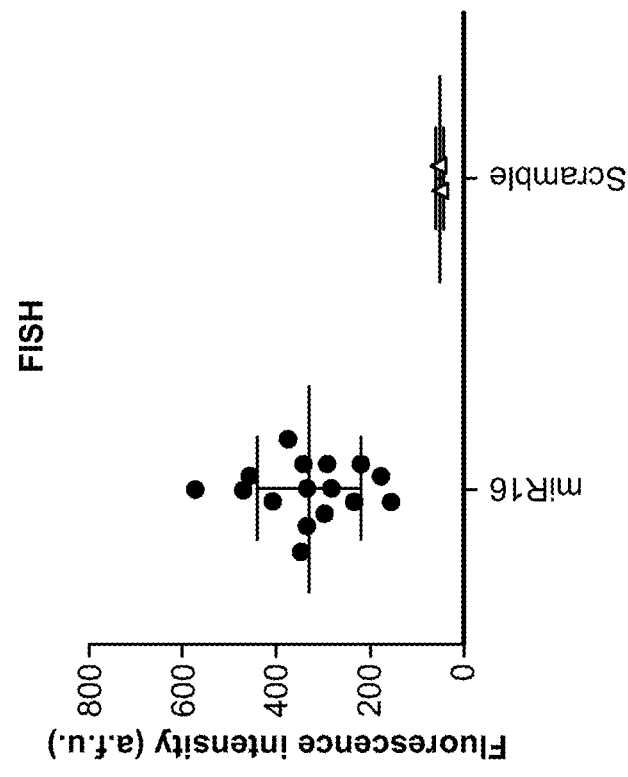

This example validates the single cell assay of the disclosure for detecting miR16 using fluorescence in situ hybridization (FISH) and a quantification of the fluorescence intensity in each of FIG. 14A and FIG. 14B. MiR16 is among the strongest signals detected and the miRNA FISH confirms the abundance in THP-1 cells. Scrambled FISH probes were used as negative control. Nuclei were visualized with 4,6-Diamidino-2-phenylindole (DAPI). See FIGS. 14A-14C.

TABLE 1

| List of miRNA targets and their sequences | | |
|---|---|---|
| 1. miR-146a-5p | UGAGAACUGAAUUCCAUGGGUU | (SEQ ID NO: 1) |
| 2. miR-145-5p | GUCCAGUUUUCCCAGGAAUCCCU | (SEQ ID NO: 2) |
| 3. miR-21-5p | UAGCUUAUCAGACUGAUGUUGA | (SEQ ID NO: 3) |
| 4. miR-16-5p | UAGCAGCACGUAAAUAUUGGCG | (SEQ ID NO: 4) |
| 5. miR-150-5p | UCUCCCAACCCUUGUACCAGUG | (SEQ ID NO: 5) |
| 6. miR-142-3p | CAUAAAGUAGAAAGCACUACU | (SEQ ID NO: 6) |
| 7. miR-155-5p | UUAAUGCUAAUCGUGAUAGGGGU | (SEQ ID NO: 7) |
| 8. miR-223-3p | UGUCAGUUUGUCAAAUACCCCA | (SEQ ID NO: 8) |
| 9. miR-424-5p | CAGCAGCAAUUCAUGUUUUGAA | (SEQ ID NO: 9) |
| 10. miR-28-5p | AAGGAGCUCACAGUCUAUUGAG | (SEQ ID NO: 10) |
| 11. miR-122-5p | UGGAGUGUGACAAUGGUGUUUG | (SEQ ID NO: 11) |
| 12. miR-221-3p | AGCUACAUUGUCUGCUGGGUUUC | (SEQ ID NO: 12) |

TABLE 2

List of DNA reporter (A-M)/miRNA capture sequence (miRNA 1-13) conjugates.

1, miR-146a/A
5' biotin-AAA AAA AAA AAA ATA CGG ACT TAG CTC CAG GAT AAA AAA-PG Linker-
AAA AAA GAT ATA TTT TAA ACC CAT GGA ATT CAG TTG TCA/3InvdT/ (SEQ ID NO: 13)

2, miR-145/B
5' biotin AAA AAA AAA AAA ATA GGC ATG ATT CAA TGA GGC AAA AAA-PC Linker-AAA
AAA AAA GAT ATA TTT TAA GGG ATT CCT GGG AAA ACT GGA C/3InvdT/ (SEQ ID NO: 14)

3, miR-21/C
5' biotin-AAA AAA AAA AAA GCG ATA GTA GAC GAG TGC AAA AAA-PC Linker-AAA
AAA AAA GAT ATA TTT TAT CAA CAT CAG TCT GAT AAG CTA/3InvdT/ (SEQ ID NO: 15)

4, hsa-miR-16-5p/D
5' biotin AAA AAA AAA AAA ATA CTC TGA CAT CTC GAC CAT AAA AAA-PC Linker-AAA
AAA CGCCAATATTTACGTGCTGCTA/3InvdT/ (SEQ ID NO: 16)

TABLE 2-continued

List of DNA reporter (A-M)/miRNA capture sequence (miRNA 1-13) conjugates.

5, hsa-miR-150-5p/E
5' biotin AAA AAA AAA AAA ATA GAT ACT GCC ACT TCA CAT AAA AAA-PC Linker-AAA
AAA ACTGGTACAAGGGTTGGGAGA/3InvdT/ (SEQ ID NO: 17)

6, hsa-miR-142-3p/F
5' biotin AAA AAA AAA AAA ATA CCG TGA ACC TTA CCT GAT AAA AAA-PC Linker-AAA
AAA TCCATAAAGTAGGAAACACTACA/3InvdT/ (SEQ ID NO: 18)

7, hsa-miR-155-5p/G
5' biotin AAA AAA AAA AAA TGC TCG GGA AGG CTA CTC AAA AAA-PC Linker-AAA
AAA CCTATCACGATTAGCATTA/3InvdT/ (SEQ ID NO: 19)

8, hsa-miR-223-3p/H
5' biotin AAA AAA AAA AAA ACG CAC CGC AGT TTG GTC AAT AAA AAA-PC Linker-AAA
AAA TGGGGTATTTGACAAACTGACA/3InvdT/ (SEQ ID NO: 20)

9, hsa-miR-424-5p/I
5' biotin AAA AAA AAA AAA ATC CGA CGC AAC AAT AGG GCA AAA AAA-PC Linker-
AAA AAA TTCAAAACATGAATTGCTGCT/3InvdT/ (SEQ lD NO: 21)

10, hsa-miR-28-5p/J
5' biotin AAA AAA AAA AAA ACC TGC TCG ACA ACT AGA AGA AAA AAA-PC Linker-AAA
AAA TCA ATA GAC TGT GAG CTC CT/3InvdT/ (SEQ ID NO: 22)

11, hsa-miR-122-5p/K
5' biotin AAA AAA AAA AAA ACC GCG ACC AGA ATT AGA TTA AAA AAA-PC Linker-AAA
AAA AAACACCATTGTCACACTCCA/3InvdT/ (SEQ ID NO: 23)

12, hsa-miR-221-3p/L
5' biotin AAA AAA AAA AAA AGC CGA AGC AGA CTT AAT CAC AAA AAA-PC Linker-AAA
AAA GAT ATA TTT TAG AAA CCC AGC AGA CAA TGT AGC T/3InvdT/ (SEQ ID NO: 24)

13, Control: miSpike/M
5' biotin AAA AAA AAA AAA AAC AGG TTG AGA ATC CTC GAC AAA AAA-PC Linker-AAA
AAA GAT ATA TTT TAA GAC CGC TCC GCC ATC CTG AG/3InvdT (SEQ ID NO: 25)

TABLE 3

List of capture DNA probes and their sequences.

A'→1: miR-146a
(SEQ ID NO: 26)
5'-AAA AAA AAA AAA AAT CCT GGA GCT AAG TCC GTA-3'

B'→2: miR-145
(SEQ ID NO: 27)
5'-AAA AAA AAA AAA AGC CTC ATT GAA TCA TGC CTA-3'

C'→3: miR-21
(SEQ ID NO: 28)
5'-AAA AAA AAA AAA AGC ACT CGT CTA CTA TCG CTA-3'

D'→4: miR-16
(SEQ ID NO: 29)
5'-AAA AAA AAA AAA AAT GGT CGA GAT GTC AGA GTA-3'

E'→5: miR-150
(SEQ ID NO: 30)
5'-AAA AAA AAA AAA AAT GTG AAG TGG CAG TAT CTA-3'

F'→6: miR-142
(SEQ ID NO: 31)
5'-AAA AAA AAA AAA AAT CAG GTA AGG TTC ACG GTA-3'

G'→7: miR-155
(SEQ ID NO: 32)
5'-AAA AAA AAA AAA AGA GTA GCC TTC CCG AGC ATT-3'

H'→8: miR-223
(SEQ ID NO: 33)
5'-AAA AAA AAA AAA AAT TGA CCA AAC TGC GGT GCG-3'

TABLE 3-continued

List of capture DNA probes and their sequences.

I'→9: miR-424
(SEQ ID NO: 34)
5'-AAA AAA AAA ATG CCC TAT TGT TGC GTC GGA-3'

J'→10: miR-28
(SEQ ID NO: 35)
5'-AAA AAA AAA ATC TTC TAG TTG TCG AGC AGG-3'

K'→11: miR-122
(SEQ ID NO: 36)
5'-AAA AAA AAA ATA ATC TAA TTC TGG TCG CGG-3'

L'→12: miR-221
(SEQ ID NO: 37)
5'-AAA AAA AAA AGT GAT TAA GTC TGC TTC GGC-3'

M'→13: Control/miSpike
(SEQ ID NO: 38)
5'-Cy3-AAA AAA AAA AGT CGA GGA TTC TGA ACC TGT-3'

What is claimed is:

1. A method comprising:
   (a) contacting cells that comprise nucleic acid targets with at least two conjugates, each conjugate comprising (i) a nucleic acid bait strand linked to (ii) a nucleic acid reporter strand through (iii) a cleavable linker, wherein the nucleic acid bait strand contains a nucleotide sequence complementary to a nucleic acid target of interest, to produce modified cells comprising target-conjugate complexes;
   (b) loading modified cells of step (a) on a base substrate containing microwells to produce a loaded base substrate, and
   (c) contacting the loaded base substrate with a cover substrate comprising at least two sets of at least two immobilized nucleic acid capture probes to produce at least two enclosed microwells,
      wherein (i) each of the capture probes of step (c) comprises a nucleotide sequence complementary to a nucleotide sequence of a nucleic acid reporter strand of step (a), (ii) each of the at least two enclosed microwells comprises a set of at least two different capture probes of the cover substrate, and (iii) each capture probe of the set of at least two different capture probes of the cover substrate corresponds to a different nucleic acid reporter strand associated with a different nucleic acid target of interest in the cells of step (a).

2. The method of claim 1, further comprising (d) cleaving the cleavable linkers of the conjugates to release the nucleic acid reporter strands.

3. The method of claim 1, further comprising maintaining the enclosed microwells under nucleic acid hybridization conditions to produce reporter-capture complexes immobilized on the cover substrate.

4. The method of claim 3, further comprising dissociating the cover substrate containing the immobilized reporter-capture complexes from the base substrate and visualizing at least one reporter-capture complex immobilized on the cover substrate.

5. The method of claim 4, further comprising identifying at least one nucleic acid target of interest of step (a).

6. The method of claim 1, wherein step (a) comprises contacting cells that comprise nucleic acid targets with at least three conjugates.

7. The method of claim 6, wherein step (a) comprises contacting cells that comprise nucleic acid targets with at least five conjugates.

8. The method of claim 7, wherein step (a) comprises contacting cells that comprise nucleic acid targets with at least ten conjugates.

9. The method of claim 1, wherein the cells are permeabilized or fixed.

10. The method of claim 1, wherein the nucleic acid bait strand contains a nucleotide sequence complementary to a ribonucleic acid (RNA) target.

11. The method of claim 10, wherein the RNA target is selected from mRNA targets, tRNA targets, rRNA targets and miRNA targets.

12. The method of claim 1, wherein the nucleic acid bait strand contains a nucleotide sequence complementary to a deoxyribonucleic acid (DNA) target.

13. The method of claim 1, wherein the cleavable linker is selected from photocleavable linkers and enzyme-cleavable linkers.

14. The method of claim 1, wherein the nucleic acid reporter strand is linked to a detectable label.

15. The method of claim 1, wherein the base substrate is a microchip.

16. The method of claim 1, wherein each microwell has a volume of 1-999 nanoliters.

17. The method of claim 1, wherein the cover substrate forms a seal with the base substrate to prevent fluid communication among the enclosed microwells.

18. A device comprising:
   (a) a base substrate comprising microwells, each microwell containing at least one cell containing at least two target-conjugate complexes, each complex comprising a nucleic acid target bound to a nucleic acid bait strand linked to a nucleic acid reporter strand through a cleavable linker; and
   (b) a cover substrate comprising at least two sets of at least two immobilized nucleic acid capture probes, each capture probe comprising a nucleotide sequence complementary to a nucleotide sequence of a nucleic acid reporter strand of (a), wherein the cover substrate is in contact with the base substrate to form at least two enclosed microwells, each of the at least two enclosed microwells containing a set of at least two different capture probes of the cover substrate, and each capture probe of the set of at least two different capture probes corresponds to a different nucleic acid reporter strand associated with a different cellular target.

19. The method of claim 1, wherein the at least two sets of at least two immobilized nucleic acid capture probes are patterned on the cover substrate.

20. The method of claim 19, wherein each of the enclosed microwells comprises at least one patterned set of the at least two immobilized nucleic acid capture probes.

* * * * *